US012617837B2

(12) United States Patent
Shibuya et al.

(10) Patent No.: US 12,617,837 B2
(45) Date of Patent: May 5, 2026

(54) COMPOSITION FOR USE IN TREATMENT OF ALLERGIC DISEASES

(71) Applicant: UNIVERSITY OF TSUKUBA, Tsukuba (JP)

(72) Inventors: Akira Shibuya, Ibaraki (JP); Kazumasa Kanemaru, Ibaraki (JP)

(73) Assignee: UNIVERSITY OF TSUKUBA, Tsukuba (JP)

( * ) Notice: Subject to any disclaimer, the term of this patent is extended or adjusted under 35 U.S.C. 154(b) by 1282 days.

(21) Appl. No.: 17/435,175

(22) PCT Filed: Feb. 28, 2020

(86) PCT No.: PCT/JP2020/008427
§ 371 (c)(1),
(2) Date: Aug. 31, 2021

(87) PCT Pub. No.: WO2020/179700
PCT Pub. Date: Sep. 10, 2020

(65) Prior Publication Data
US 2022/0153806 A1 May 19, 2022

(30) Foreign Application Priority Data

Mar. 1, 2019 (JP) ................................. 2019-037353
Apr. 26, 2019 (JP) ................................. 2019-086233

(51) Int. Cl.
*C07K 14/705* (2006.01)
*A61K 35/17* (2025.01)
(Continued)

(52) U.S. Cl.
CPC .......... *C07K 14/7056* (2013.01); *A61K 35/17* (2013.01); *C12N 15/86* (2013.01);
(Continued)

(58) Field of Classification Search
CPC ............ C07K 14/7056; C07K 2319/02; C07K 2319/03; C07K 2319/30; C07K 14/7051;
(Continued)

(56) References Cited

U.S. PATENT DOCUMENTS

2010/0221265 A1    9/2010   Sancho-Madrid et al.
2010/0306863 A1   12/2010   Colonna et al.
(Continued)

FOREIGN PATENT DOCUMENTS

JP    2010-534200 A    11/2010
JP    2010-534828 A    11/2010
JP    2017-507945 A     3/2017

OTHER PUBLICATIONS

Parry (Parry, Alison L., et al. "Multicopy multivalent'glycopolymer-stabilized gold nanoparticles as potential synthetic cancer vaccines." Journal of the American Chemical Society 135.25 (2013): 9362-9365.) (Year: 2013).*

(Continued)

*Primary Examiner* — Tracy Vivlemore
*Assistant Examiner* — Thomas R. Amick
(74) *Attorney, Agent, or Firm* — Oblon, McClelland, Maier & Neustadt, L.L.P.

(57) ABSTRACT

The present invention provides a composition and method for treating an allergic disease. The composition comprises a ligand for asialoglycoprotein receptor 1 (Asgr1). The allergic disease may be atopic dermatitis, allergic rhinitis, urticaria, allergic asthma, allergic conjunctivitis, allergic gastrointestinal inflammation, or anaphylactic shock. The allergic disease may be caused by house dust mites. The present invention also provides a method for determining if a test compound activates human Asgr1.

12 Claims, 14 Drawing Sheets

Specification includes a Sequence Listing.

(51) Int. Cl.
 *A61K 38/00* (2006.01)
 *C12N 15/86* (2006.01)
(52) U.S. Cl.
 CPC .......... *A61K 38/00* (2013.01); *C07K 2319/02* (2013.01); *C07K 2319/03* (2013.01); *C07K 2319/30* (2013.01)
(58) Field of Classification Search
 CPC .... A61K 35/17; A61K 38/00; A61K 38/1735; A61K 39/35; C12N 15/86; C12N 15/62; A61P 1/04; A61P 11/02; A61P 11/06; A61P 17/00; A61P 17/04; A61P 27/02; A61P 27/14; A61P 27/16; A61P 37/08
 See application file for complete search history.

(56) References Cited

U.S. PATENT DOCUMENTS

| | | |
|---|---|---|
| 2013/0024961 A1 | 1/2013 | Burlak et al. |
| 2017/0073413 A1 | 3/2017 | Bebbington et al. |
| 2017/0106051 A1 | 4/2017 | Oh et al. |
| 2021/0299224 A1 | 9/2021 | Oh et al. |

OTHER PUBLICATIONS

Partial Supplementary European Search Report issued Nov. 15, 2022, in corresponding European Patent Application No. 20765494. 8, 14 pages.
D'Souza Anisha A. et al: "Asialoglycoprotein receptor mediated hepatocyte targeting—Strategies and applications", Journal of Controlled Release, Elsevier, vol. 203, Feb. 18, 2015, pp. 126-139, XP029149040.
Cote Robert et al: "CLEC receptors, endocytosis and calcium signaling", Aims Allergy and Immunology, vol. 1, No. 4, Jan. 1, 2017, pp. 207-231, XP055977892.
M. G. Wahrenbrock: "Multiple Hepatic Receptors Cooperate to Eliminate Secretory Mucins Aberrantly Entering the Bloodstream: Are Circulating Cancer Mucins the "Tip of the Iceberg"?", Cancer Research, vol. 66, No. 4, Feb. 15, 2006, pp. 2433-2441, XP055065451.

Kanemaru Kazumasa et al: "Clec10a suppresses house dust mite-induced dermatitis (Mo-P3-9)", Cytokine, vol. 100, Dec. 1, 2017, p. 90, XP055977584, 118 pages.
Drinić, Mirjana et al., "*Toxoplasma gondii* tachyzoite-extract acts as a potent immunomodulator against allergic sensitization and airway inflammation," Scientific Reports, vol. 7, No. 1, Nov. 9, 2017, 12 pages. XP093228974.
Bandini, Giulia et al., "Protein O- and C-Glycosylation pathways in *Toxoplasma gondii* and *Plasmodium falciparum*", Parasitology, vol. 146, No. 14, Dec. 1, 2019, pp. 1755-1766, XP093228976.
European Office Action issued Dec. 4, 2024 in European Patent Application No. 20765494.8, 8 pages.
International Search Report issued May 26, 2020 in PCT/JP2020/008427 (with English Translation), 6 pages.
International Preliminary Report on Patentability and Written Opinion issued Jan. 6, 2021 in PCT/JP2020/008427 (with English Translation), 14 pages.
Katoh, Toshihiko, "Inhibition mechanism of inflammation through the inter action between siglec and mucin sugar chains, Role of mucin sugar chains in allergic immune response", Kagaku To Seibutsu, 2016, vol. 54, No. 6, pp. 375-376, 2016, ISSN: 1883-6852) (with English Translation).
Kakuta, Yoshiya et al., "Glycans carried by airway mucins are endogenous ligands for Siglec-F and induce eosinophil apoptosis", Clinical immunology & allergology, 2016, vol. 65, no. 5, pp. 468-471, ISSN: 1881-7930 (with English Translation).
Kanemaru, K. et al., "Clec10a regulates mite-induced dermatitis", Sci Immunol, vol. 4, No. 42, Dec. 6, 2019, Article No. eaax6908, pp. 1-14 and cover page.
Thomas Bieber, "Atopic Dermatitis", The new England Journal of Medicine, Apr. 3, 2008, pp. 1483-1494.
Alain Jacquet, "The role of innate immunity activation in house dust mite allergy", Trends in Molecular Medicine, vol. 17, No. 10, Oct. 2011, pp. 604-611.
Mina Yamamoto et al., "Contribution of itch-associated scratch behavior to the development of skin lesions in *Dermatophagoides farinae*-induced dermatitis model in NC/Nga mice", Arch Dermatol Res (2009) 301, pp. 739-746.
J. Kenneth Hoober, "ASGR1 and Its Enigmatic Relative, CLEC10A", Int. J. Mol. Sci., 2020, 21, 4818, p. 1-20.

* cited by examiner

LA-glycan

Clec10a-L
derived from HDM

↓

Lectin array
(up to 96 lectins)

↓

Binding profile
for lectin
→ prediction of
glycan in Clec10a-L

GA-glycan

Clec10a-Fc

↓

Glycan array
(up to 70 glycans)

↓

Glycan to which
Clec10a-Fc binds

LA-glycan          GA-glycan

Terminal Gal (+): 5 glycans

↓

+ manual curation
→ 7 glycans

Remove tape and administer 50 µg LPS and glycan daily

Histological analysis on Day 5

Tn antigen     T antigen

Ser/Thr          Ser/Thr

: GalNAc

○ : Galactose wherein Ser/Thr represents a serine or threonine residue.

where T antigen represents Gal$\beta$1-3GalNAc$\alpha$1; Gal$\alpha$1-3LN represents Gal$\alpha$1-3Gal$\beta$1-4GlcNAc$\beta$1; Gal$\alpha$1-4LN represents Gal$\alpha$1-4Gal$\beta$1-4GlcNAc$\beta$1; LeA represents Gal$\beta$1-3(Fuc$\alpha$1-4)GlcNAc$\beta$1; and LeX represents Gal$\beta$1-4(Fuc$\alpha$1-3)GlcNAc$\beta$1.

COMPOSITION FOR USE IN TREATMENT OF ALLERGIC DISEASES

TECHNICAL FIELD

The present invention relates to a composition for use in treatment of an allergic disease.

BACKGROUND ART

House dust mites (HDMs) are major allergens of allergic diseases such as atopic dermatitis and asthma (Non Patent Literatures 1 and 2). NC/Nga mouse is a mouse strain which is sensitive to HDM and develop more severe dermatitis due to HDM as compared with other strains (Non Patent Literature 3). However, a mechanism of pathogenesis of dermatitis is largely unknown.

CITATION LIST

Patent Literature

Non Patent Literature 1: Bieber, T. N. Engl. J. Med., 358: 1483-1494, 2008

Non Patent Literature 2: Jacquet, A., Trends Mol. Med., 17: 604-611, 2011

Non Patent Literature 3: Yamamoto, M. et al., Arch. Dermatol. Res., 301: 739-746, 2009

SUMMARY OF INVENTION

The present invention provides a composition for use in treatment of an allergic disease.

The present inventors discovered that Clec10a is involved in the development and exacerbation of dermatitis due to house dust mites in mice. The present inventors also discovered that, in humans a structural functional counterpart of Clec10a is Asgr1, and also, in humans, Asgr1 is involved in the development and exacerbation of dermatitis by house dust mites. The present inventors further discovered that house dust mites contain a substance which binds to mouse Clec10a and human Asgr1 and which suppresses the development of allergies (e.g., Clec10a ligand or Asgr1 ligand). The present inventors further discovered that the Clec10a ligand includes an O-linked glycan, in particular, a T antigen (Galβ(1-3)GalNAc) or a Tn antigen (αGalNAc), and that ASGR1 binds to both of them. The present invention is based on these findings.

That is, the present invention provides, for example, the following inventions.

(1) A composition for use in treatment of an allergic disease, the composition including a ligand for asialoglycoprotein receptor 1 (Asgr1).

(2) The composition according to (1), wherein the allergic disease is one or more selected from the group consisting of atopic dermatitis, allergic rhinitis, urticaria, allergic asthma, allergic conjunctivitis, allergic gastrointestinal inflammation and anaphylactic shock.

(3) The composition according to (1) or (2), wherein the allergic disease is caused by a house dust mite.

(4) The composition according to any one of (1) to (3), wherein the ligand includes either or both of a T antigen and a Tn antigen.

(5) The composition according to any one of (1) to (3), wherein the ligand is a glycan selected from the group consisting of a T antigen and a Tn antigen.

(6) The composition according to any one of (1) to (4), wherein the ligand is a mucin-like protein or mucin.

(7) The composition according to any one of (1) to (6), wherein the ligand is a ligand for human asialoglycoprotein receptor 1.

The present invention also provides the following inventions.

(1A) A composition for use in treatment of an allergic disease, including a ligand for asialoglycoprotein receptor 1 (Asgr1).

(2A) The composition according to (1A), wherein the allergic disease is one or more selected from the group consisting of atopic dermatitis, allergic rhinitis, urticaria, allergic asthma, allergic conjunctivitis, allergic gastrointestinal inflammation and anaphylactic shock.

(3A) The composition according to (1A) or (2A), wherein the allergic disease is caused by a house dust mite.

(4A) The composition according to any one of (1A) to (3A), wherein the ligand includes at least one glycan selected from the group consisting of a T antigen, a Tn antigen, LeA, and Lex.

(5A) The composition according to any of (1A) to (3A), wherein the ligand includes a polymeric scaffold presenting at least one glycan selected from the group consisting of a T antigen, a Tn antigen, LeA, and Lex.

(6A) The composition according to any one of (1A) to (4A), wherein the ligand is a mucin-like protein or mucin.

(7A) The composition according to any one of (1A) to (6A), wherein the ligand is a ligand for human asialoglycoprotein receptor 1.

(8A) An animal cell expressing a fusion protein including an extracellular region and a transmembrane region of human asialoglycoprotein receptor 1, and an intracellular region of CD3ζ, the animal cell having a gene encoding a reporter operably linked to a promoter activated by a CD3ζ signal.

(9A) A method of testing that a test compound is a compound that activates human asialoglycoprotein receptor 1, the method including:

contacting the cell described in (8A) with a test compound; and determining that the test compound is a compound that binds to human asialoglycoprotein receptor 1 when a reporter expression level is enhanced.

BRIEF DESCRIPTION OF DRAWINGS

FIG. 13 shows results of a reporter assay using Clec10a reporter cells to examine whether polymeric scaffolds presenting indicated different glycans activated Clec10a.

DETAILED DESCRIPTION OF THE INVENTION

Figure 1:
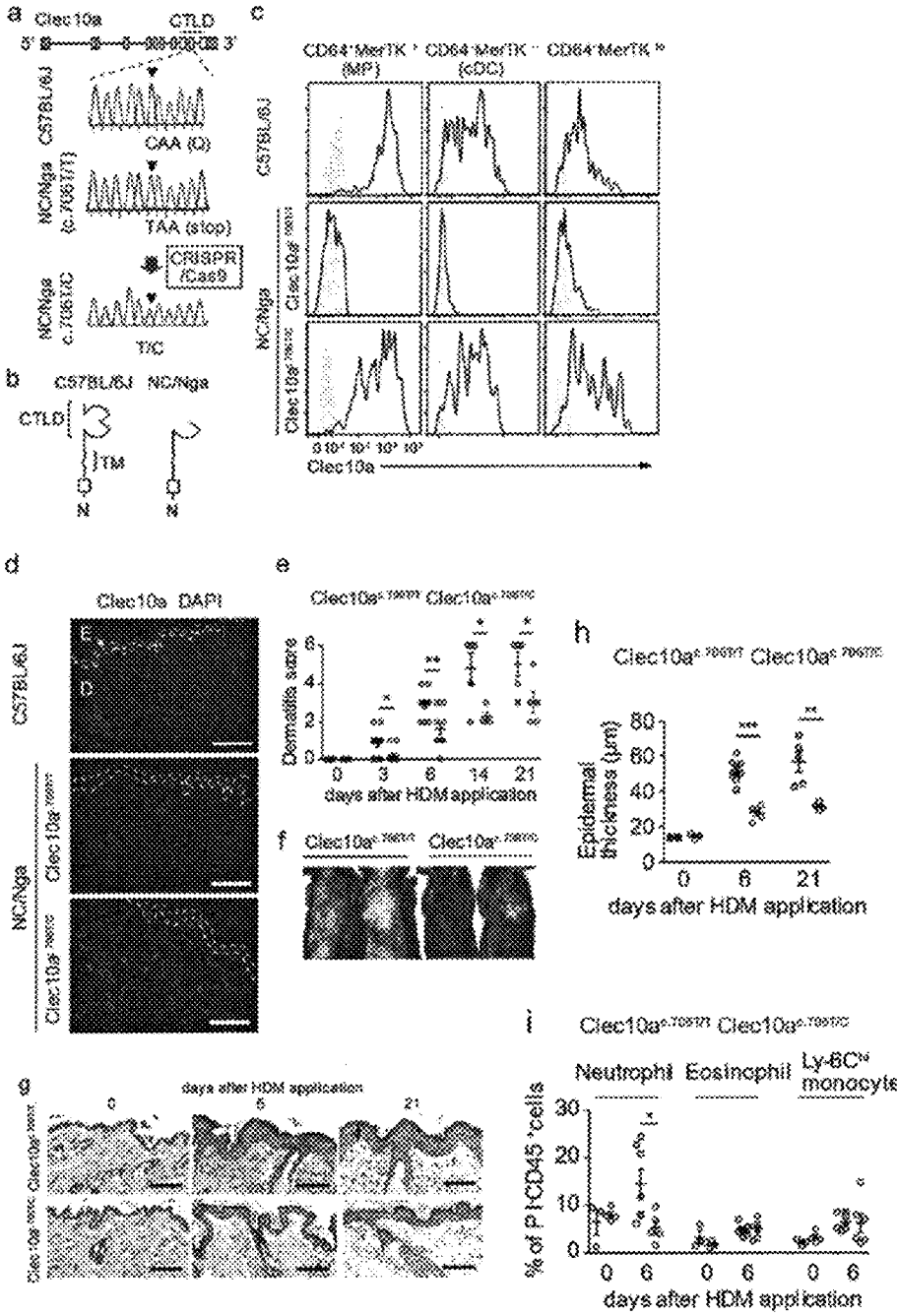
FIG. 1 shows that a nonsense mutation in Clec10a in NC/Nga mice causes HDM-induced dermatitis. Panel a shows Clec10a genes and DNA sequences of nonsense mutation sites (c.706) in C57BL/6J Clec10a (NM_010796), NC/Nga-Clec10a$^{c.706T/T}$ (c.706T/T), and NC/Nga-Clec10a$^{c.706\ T/C}$ (c.706T/C) mice. The total length of Clec10a is represented by a plurality of open squares and lines therethrough, with open squares representing coding regions of the genes and lines showing introns. CUD represents a c-type lectin-like domain. Panel b shows a schematic representation of Clec10a for each of the C57BL/6J mice and the NC/C57BL/6 mice. TM represents a transmembrane domain. Panel c shows expression of Clec10a on a cell surface of macrophages (MPs) (CD64+MerTK+), known DCs (cDCs) (CD64-MerTK−), and monocyte-derived dendritic cells (CD64-MerTK$^{lo}$) in PI-CD45+ MHCII+Lineage (CD3, CD19, NK1.1, and Ly-6G)-EpCAM− cells on the dorsal skin of C57BL/6J mice, NC/Nga-Clec10a$^{c.706T/T}$ mice, and NC/Nga-Clec10a$^{c.706T/C}$ mice. A shaded histogram shows staining with an isotype control antibody (Ab). Panel d shows fluorescence microscopy images of tissue sections of the dorsal skin of C57BL/6J mice, NC/Nga-Clec10a$^{c.706T/T}$ mice, and NC/Nga-Clec10a$^{c.706T/C}$ mice. The tissue sections were stained with an anti-Clec10a monoclonal antibody (mAb) and 4',6-di-amidino-2 phenylindole (DAPI). E represents the epidermis, and D represents the dermis. The scale bar indicates 100 μm. Panels e to i show results of applying an HDM ointment twice a week to the dorsal skin of NC/Nga-Clec10a$^{c.706T/T}$ mice, NC/Nga-Clec10a$^{c.706T/C}$ mice. Panel e shows dermatitis scores, Panel f shows appearance on Day 14, Panels g and h show tissue sections (hematoxylin and eosin stained) and epithelial thickness, respectively. Panel i shows the total number of individuals with neutrophils (CD11b$^+$Ly-6G$^+$), eosinophils (CD11b$^+$Siglec-F$^+$), and Ly-6C$^{hi}$ monocytes (CD11b$^+$Ly-6$^G$-Siglec-F$^-$Ly-6C$^{hi}$). * represents $p<0.05$,  represents $p<0.01$, and * represents $p<0.001$ (independent two-sided Student's t-test). Data indicates mean±SEM.

Herein, "subject" may be a mammal, including, for example, pets such as dogs, cats, rabbits, hamsters, guinea pigs, and squirrels; livestock such as cows, pigs, horses, sheep, and goats; and primates such as monkeys, chimpanzees, orangutans, gorillas, bonobos, and humans.

"Treatment" is used herein in the sense including therapeutic and prophylactic treatments. Treatment may be used herein in the sense including suppressing a disease or deterioration of a condition, delaying a disease or deterioration of a condition, improving a disease or a condition, or healing of a disease or a condition. Prevention may be used herein in the sense suppressing onset of a disease or a condition or delaying onset of a disease or a condition.

Herein, "allergy" means a systemic or local disorder with respect to a living organism based on an immune response. Allergies are broadly divided into allergies (type I, type II, and type III) based on humoral immune response by blood antibodies and allergies (type IV) based on cellular immunity by sensitized lymphocytes.

Type I allergies are allergies also called immediate allergies or anaphylactic types. IgE is involved in type I allergies, and, when IgE binds with IgE receptors (FcεRI) located on the cell surface of mast cells or basophils in the blood or tissue, and an allergen binds thereto, a chemical mediator such as histamine is released from the mast cells or basophils, thereby causing allergic reactions (e.g., smooth muscle contraction, vascular hyperpermeability, and glandular hypersecretion). Type I allergies include atopic bronchial asthma, allergic rhinitis, urticaria, allergic conjunctivitis, atopic dermatitis, and anaphylactic shock. It is known that, in type I allergies, housing dust, mites, and the like enter the body and cause an allergic reaction (which may enter via routes such as oral route, inhalation route, transdermal route, and transvenous route).

Type II allergies are based on cytotoxicity caused by reaction of IgG or IgM with cells, tissue antigens, and the like and binding of a complement thereto. Antibody-dependent cellular cytotoxicity (ADCC) in which macrophages, killer cells and the like having IgG Fc receptors bind to IgG bound to an antigen of the cell membrane and damage the cells are also included in type II allergies. Type II allergies include hemolytic anemia due to incompatible blood transfusion, autoimmune hemolytic anemia, idiopathic thrombocytopenic purpura, drug-induced hemolytic anemia, granulocytopenia, thrombocytopenia, and Goodpasture's syndrome. Type III allergies are also called immunocomplex type or Arthus type, and are based on tissue damage by the immunocomplex of a soluble antigen with IgG or IgM. Type III allergies include serum disease, autoimmune diseases such as systemic lupus erythematosus and rheumatoid arthritis, glomerulonephritis, hypersensitivity pneumonia, allergic bronchopulmonary aspergillosis. Type IV allergies are also called delayed allergies, and are based on reaction of sensitized T cells with an antigen to release cytokines from the sensitized T cells, resulting in cytotoxicity. Type IV allergies are also based on virus-infected cells by killer T cells, tumor cells, and impairment to grafts. Type IV allergies include allergic contact dermatitis, atopic dermatitis, hypersensitivity pneumonia, tuberculous cavities, leprosy, epithelioid cell granuloma lesions of sarcoidosis, smallpox rash, and measles rash.

Herein, "asialoglycoprotein receptor" is a receptor that binds to a glycoprotein wherein sialic acid at a terminal end of a glycan of a protein is removed and the inner galactose residue is exposed as a terminal group, i.e., an asialoglycoprotein (AGP). The asialoglycoprotein receptor is present on a surface of hepatocytes and binds to AGP in the blood to remove the AGP from the blood. Asialoglycoprotein receptor 1 (ASGR1) is also called C-type lectin domain family member H1 or CLEC4H1. A representative example of human ASGR1 protein can be a protein having an amino acid sequence registered with GenBank under registration number CAG46849.1. "ASGR1", as used herein, is used in the sense including an ortholog of human ASGR1.

Herein, "Clec10a" is also called C-type lectin domain family 10, member A, which is a molecule that recognizes glycans and functions as a host's biological defense system. Clec10a can specifically bind to galactose or N-acetylgalactosamine.

In the present specification, "house dust mite" is a mite belonging to the genus *Dermatophagoides*. Main species of house dust mites are *Dermatophagoides farinae, Dermatophagoides microceras, Dermatophagoides pteronyssinus*, and *Euroglyphus maynei*.

"Antigen", as used herein, means a substance that provides an epitope with which a lectin may be reacted in the case of antibodies or sugars. In the context of glycans, "antigen" means a glycan that provides an epitope with which a lectin may be reacted, in accordance with its ordinary word meaning. Thus, when used in the context of glycans, "antigen" means providing a glycan to a skin surface of the glycan as an epitope with which a lectin may be reacted, as is found in natural glycans and glycoproteins.

Herein, "ligand" refers to a counterpart substance to which the receptor binds. The ligand may control a downstream signal of a receptor by binding to the receptor. Herein, substances that positively regulate downstream signals of receptors are called "agonists." Herein, substances that negatively regulate downstream signals of receptors are called "antagonists."

Herein, "GalNAc" means N-acetylgalactosamine, and "GlcNAc" means N-acetylglucosamine.

The present inventors discovered that Clec10a is involved in the onset and exacerbation of dermatitis due to house dust mites in mice and that Asgr1 is involved therein in humans. From the results of functional analysis and homology analysis, the present inventors also discovered that human Asgr1 is an original structural and functional counterpart of mouse Clec10a. The present inventors also discovered that the house dust mites include a substance that binds to and activates mouse Clec10a and human Asgr1 and suppresses development of an allergy (e.g., Clec10a ligand or Asgr1 ligand). The present inventors further discovered that the Clec10a ligand includes an O-linked glycan, in particular, a T antigen (Galβ(1-3)GalNAc) or a Tn antigen (αGalNAc), and that ASGR1 binds to both of them. The present inventors also discovered that the Clec10a ligand suppresses TLR4 signals.

Figure 15:
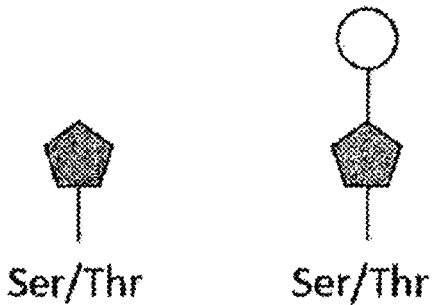
FIG. 15 shows a structure of the T antigen (Galβ(1-3)GalNAc) and the Tn antigen (aGalNAc).
Figure 15:

The T antigen (Galβ(1-3)GalNAc) and the Tn antigen (αGalNAc) are each a glycan having a structure as shown in FIG. 15. Binding of Asgr1 to a T antigen and a Tn antigen is consistent with Asgr1 having affinity for galactose or N-acetylgalactosamine.

Figure 16:
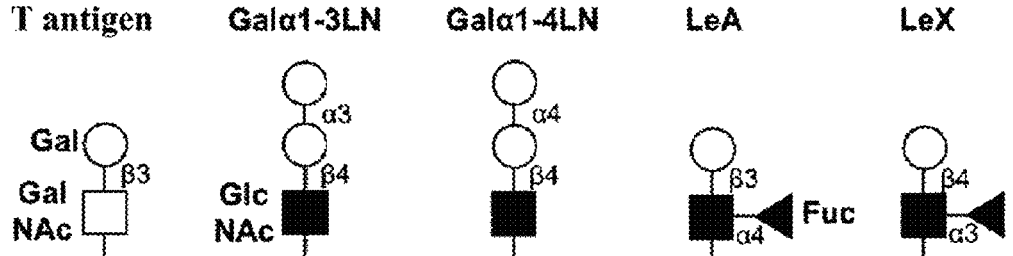
FIG. 16 shows structures of T antigen, Galα1-3LN, Galα1-4LN, LeA, and LeX.

Asgr1 also binds to a glycan selected from the group consisting of a T antigen, LeA, and a LeX, thereby transmitting signals into cells. FIG. 16 shows structures of T antigen, Galα1-3LN, Galα1-4LN, LeA, and LeX.

The glycans may be presented on the polymeric scaffold. For example, the glycans may be linked on side chains of polymeric scaffolds having, as their backbone, biocompatible polymers such as polylactic acid, polyacrylamide, polyvinyl, polyvinyl alcohol, polymethyl methacrylate, polyacrylonitrile, polystyrene, polypropylene, polyethylene terephthalate, nylon, collagen, hydroxyethyl methacrylate, chitosan, chitin, polyethylene oxide, polyethylene glycol, polyamino acid, polylactide, polyglycolide, polycaprolactone, and copolymers thereof, and presented to Clec10a. Whether or not the glycan presented on the polymeric scaffold activates Clec10a or Asgr1 can be confirmed using CD3ζ reporter cells which will be described below. In the above, the respective polymers are not particularly limited as long as they have administrable physical properties (e.g., viscosity, osmotic pressure, etc.). For example, biocompatible polymers having a weight average molecular weight from 1 kDa to 100 kDa, from 5 kDa to 50 kDa, from 10 kDa to 40 kDa, or from 20 to 40 kD can be used as their backbone.

According to the present invention, when a nonsense mutation or a frameshift mutation was introduced into Clec10a, which is a mouse counterpart of asialoglycoprotein receptor 1 (Asgr1), the response to HDM became excessive. When extracts (purified) containing a Clec10a ligand were also prepared and contacted with human Asgr1-CD3ζ reporter cells, Asgr1 responded to the Clec10a ligand in a concentration dependent manner. This activation was also offset, in a concentration dependent manner, by the addition of galactose to the system. From this, it can be concluded that the ligand for asialoglycoprotein receptor 1 (Asgr1) can be used to treat a TLR4 signal-induced disease or symptom (e.g., inflammation and an allergic disease) such as a house dust mite-induced allergy.

Accordingly, the present invention provides a composition for use in treatment of an allergic disease, including a ligand for asialoglycoprotein receptor 1 (Asgr1). The present invention provides a composition for use in treatment of a disease or symptom (e.g., inflammation and an allergic disease) induced by activation of a TLR4 signal, including a ligand for asialoglycoprotein receptor 1 (Asgr1). The TLR signal can be activated by a TLR4 ligand. TLR4 ligand includes lipopolysaccharide (LPS) and lipoteichoic acid, and agonists that are analogs thereof. Thus, the ligand for asialoglycoprotein receptor 1 (Asgr1) can be used to treat diseases or conditions (e.g., inflammation and allergic diseases) induced by an allergen including these TLR4 ligands. Accordingly, the present invention provides a composition for use in treatment of a disease or symptom induced by an allergen including a TLR4 ligand, wherein the composition contains a ligand for asialoglycoprotein receptor 1 (Asgr1).

The ligand for asialoglycoprotein receptor 1 (Asgr1) include a glycan from which sialic acid is released and which has Lewis X at its terminal, and a protein having the glycan. The ligand for asialoglycoprotein receptor 1 (Asgr1) include a glycan from which sialic acid is released and which has a T antigen or a Tn antigen at its terminal, and a protein having the glycan. T antigen means Galβ(1-3)GalNAc, and Tn antigen means αGalNAc. The ligand for asialoglycoprotein receptor 1 (Asgr1) may be one, two or all O-linked glycans from which sialic acid is released and which is/are selected from the group consisting of a Lewis X antigen, a T antigen, and a Tn antigen at the terminal, or a protein having the glycan. The mucin-like protein has the O-linked glycan and has a glycan selected from the group consisting of a Lewis X antigen, a T antigen, and a Tn antigen. Thus, the ligand for asialoglycoprotein receptor 1 may be a mucin-like protein or mucin. The protein as the ligand for asialoglycoprotein receptor 1 (Asgr1) can be a mucin-like protein or mucin.

Asgr1 is highly expressed in hepatocytes in vivo, and aged protein (asialoglycoprotein) desialylated in vivo is taken into hepatocytes and removed from the blood. Thus, such desialylated glycoproteins may all be used as the ligand for asialoglycoprotein receptor 1. Asgr1 binds to and reacts with a glycan having at least one or both of a T antigen and a Tn antigen. Thus, a glycan having at least one or both of a T antigen and a Tn antigen or a protein having this glycan can all be used as the ligand for asialoglycoprotein receptor 1. Also, all the ligands for asialoglycoprotein receptor 1 can be obtained by affinity purification of allergen-containing substances (e.g., HDM extracts) based on binding affinity with Clec10a (e.g., mouse Clec10a or human Asgr1). Elution of the Clec10a ligand from Clec10a can be performed, for example, using galactose. A Clec10a ligand eluate may be dialyzed with saline.

Fusion proteins including an extracellular region and a transmembrane region of human asialoglycoprotein receptor 1, and an intracellular region of CD3ζ transmitted a CD3ζ signal to the downstream in the presence of the ligand for asialoglycoprotein receptor 1. Therefore, with a fusion protein including the extracellular region and the transmembrane region of human asialoglycoprotein receptor 1 and the intracellular region of CD3ζ, a substance for use in treatment of an allergic disease can be confirmed. For example, it can be confirmed that a test compound is a compound that binds to human asialoglycoprotein receptor 1 by contacting the compound with an animal cell expressing a fusion protein including the extracellular region and the transmembrane region of human asialoglycoprotein receptor 1 and the intracellular region of CD3ζ, the animal cell having a gene encoding a reporter operably linked to a promoter (for example, an NFAT promoter) that activated by a CD3ζ signal. In addition, it is possible to confirm that the obtained substance is a substance for use in treatment of an allergic disease using control signaling via inhibitory ITAM as an index.

Also, for the allergy suppressive effect of compounds (candidate compounds for the ligand for human Asgr1), for example, compounds can be applied to LPS-induced dermatitis to confirm the effect of suppressing dermatitis.

Thus, in an embodiment of the present invention, there are provided a fusion protein including an extracellular region and a transmembrane region of human asialoglycoprotein receptor 1, and an intracellular region of CD3ζ, and an animal cell that expresses the fusion protein. Also in an embodiment of the present invention, the animal cell may have a gene encoding a reporter operably linked to a promoter activated by a CD3ζ signal. In an embodiment of the present invention, there is provided a method of confirming that a test compound is a compound that binds to human asialoglycoprotein receptor 1 by contacting the compound with an animal cell expressing a fusion protein including an extracellular region and a transmembrane region of human asialoglycoprotein receptor 1, and an intracellular region of CD3ζ, the animal cell having a gene encoding a reporter operably linked to a promoter that activated by a CD3ζ signal.

In an aspect of the invention, the test compound may contain a ligand for asialoglycoprotein receptor 1 (Asgr1). In a certain aspect of the invention, a ligand of the test compound may be at least one glycan selected from the group consisting of a T antigen and a Tn antigen. In a certain aspect of the invention, the ligand may be a mucin-like protein or mucin. In a certain aspect of the invention, the ligand may be a ligand for human asialoglycoprotein receptor 1.

The animal cell expressing a fusion protein including an extracellular region and a transmembrane region of human asialoglycoprotein receptor 1, and an intracellular region of CD3ζ, the animal cell having a gene encoding a reporter operably linked to a promoter that activated by a CD3ζ signal can also be used in compound screening. Therefore, the present invention provides a method for screening for a human Asgr1 ligand or agonist, the method including contacting a test compound with an animal cell expressing a fusion protein including an extracellular region and a transmembrane region of human asialoglycoprotein receptor 1, and an intracellular region of CD3ζ, the animal cell having a gene encoding a reporter operably linked to a promoter that activated by a CD3ζ signal. When the reporter activity is observed, it indicates the test compound is a candidate for the human Asgr1 ligand or agonist.

The animal cell may preferably be a human cell.

The compositions of the present invention may be compositions such as personal care compositions and pharmaceutical compositions.

Pharmaceutical compositions include, for example, pharmaceutical compositions for topical administration and can be used in the present invention. The pharmaceutical composition for topical administration may be a pharmaceutical composition for mucosal or body surface application, and examples thereof include eye drops, eye ointments, sublingual tablets, buccal tablets, troches, gargling agents, sprays, aerosols, and inhalants; solution formulations such as solutions, irrigation agents, glycerin formulations, tartar formulations, aqueous formulations, and coating agents; dispersion formulations such as emulsions, suspensions, liniments, lotions, sprays, and liposomes; semi-solid formulations such as ointments, plasters, patches, adhesive tapes, pastas, cataplasms, cream, oil agents, and sticks; and leaching formulations such as extracts (soft extract, dry extract) and tinctures.

According to the invention, the pharmaceutical composition may contain a pharmaceutically acceptable additive. The pharmaceutically acceptable additive includes solvents, bases, diluents, volume fillers, fillers, and auxiliaries; dissolution aids, solubilizers, buffers, isotonizing agents, emulsifiers, suspending agents, dispersants, thickeners, gelling agents, curing agents, absorbents, adhesives, elastic agents, plasticizers, sustained release agents, and propellants; antioxidants, preservatives, humectants, light blocking agents, antistatic agents, fragrances, flavoring agents, coloring agents, and mitigating agents.

Personal care compositions include, for example, skin care, antiperspirant, deodorant, cosmetic, cosmetic, and hair care products. Personal care compositions include moisturizers, conditioners, anti-aging agents, whitening agents, sunscreens, antiperspirants, shaving compositions, post-shave compositions, foundations, lipsticks, lipsticks, styling compositions, shampoos, cleansers, and lubricants. The personal care composition may be used in personal care products. Personal care products include undergarments, diapers, tissues, wipes, masks, and patches. The composition may contain an additive in addition to the active ingredient. The composition can be in dosage form suitable for administration, such as intravenous administration, transdermal administration, oral administration, enteral administration, and intraperitoneal administration. For the prevention and/or treatment of dermatitis, the composition of the present invention may be administered by transdermal administration, and may be, for example, in the form of a gel, an emulsion, a cream, a liquid, a paste, a lotion, a liposome cream, or the like (for example, a dermatological composition). In an aspect, the composition may be an ointment. In the case of transdermal administration, a dermatologically acceptable additive may be used, and a dosage form suitable therefor can be used. In the case of transmucosal administration, the additive that can be used may be an additive acceptable for mucosal application, and a dosage form suitable therefor may be used.

The present invention provides use of an Asgr1 ligand in the manufacture of a composition for use in treatment of an allergic disease.

The present invention provides a method of treating an allergic disease in a subject in need thereof, including administering to the subject an effective amount of an Asgr1 ligand.

The present invention provides a method of preventing an allergic disease or suppressing development of the allergic disease, including administering to a subject an effective amount of an Asgr1 ligand.

EXAMPLES

Method (1) Preparation of Skin Cell

Skin cells were minced by pinching the thin-sculpted dorsal skin samples and incubated for 60 minutes in an RPMI-1640 medium containing 200 U/mL collagenase II, 50 U/mL DNase and 10% fetal bovine serum (FBS). Additional dissociation and homogenization were performed using gentleMACS Disociator (Miltenyi Biotec). The resulting cells were filtered through a 55-μm nylon mesh to obtain a single cell suspension.

(2) Flow Cytometry

Flow cytometry and cell sorting were performed using FACS LSRFortessa and FACS Aria (BD Biosciences), respectively. FlowJo software (Tree Star) was used for analysis of data. Dead cells were stained with propidium iodide solution (Sigma-Aldrich, P4864) and removed.

(3) Histology and Immunohistochemical Staining

For histological analysis, dorsal skin samples harvested from mice were formalin-fixed and paraffin-embedded to create 4 μm thick sections. Sections were stained with hematoxylin-eosin and analyzed by optical microscopy. Epithelial thickness was measured in five regions per mouse and at five sites per region.

For immunohistochemical staining, skin samples harvested from mice were embedded in TissueTek Optimal Cutting Temperature Compound (Sakura Finetek Japan) and stored at −80° C. Four (4) μm-thick sections were also used in immunohistochemical staining. The sections were washed with PBS containing 0.05% Tween-20 (PBS-T, pH 7.4), stained and incubated for 10 min at room temperature using Blocking One Histo (Nacalai). The sections were then washed with PBS-T, incubated overnight at 4° C. using anti-Clec10a mAb, washed with PBS-T and incubated using Alexa Fluor 546 labeled anti-rat IgG polyclonal antibody for 1 hour. After washing with PBS-T, the sections were subjected to nuclear staining with DAPI.

Human healthy skin tissue was harvested from the periphery of the patient's tumor region, formalin-fixed, paraffin-embedded into 4 μm-thick sections. The sections were deparaffinized with xylene, and rehydrated with ethanol, and endogenous peroxidase was blocked with methanol. The sections were stained with anti-CD69 antibodies and anti-Asgr1 antibodies according to the manufacturer's manual for Opal 4-Color Automation IHc Kit (PerkinElmer, NEL820001KT). Briefly, the sections were incubated at 95° C. for 15 minutes, washed with TBS (TBS-T) (Takara Bio, T9142) containing 0.05% Tween-20 and treated with a blocking solution at room temperature for 10 minutes. The sections were incubated overnight at 4° C. with anti CD68 antibodies or mouse IgG1 antibodies, washed with TBS-T and treated with Opalpolymer HRP in a wet chamber at room temperature for 30 minutes. After washing with TBS-T, the sections were incubated using Opal Fluorophore Working Solution in a wet chamber at room temperature for 10 minutes and washed with TBS-T. The antibodies for the first staining were removed from the sections by heating at 95° C. The sections were then stained with anti-CD9 antibodies or rabbit IgG antibodies as in the first staining. The sections were subjected to nuclear-staining with a spectral DAPI solution.

(4) House Dust Mite (HDM)-Induced Dermatitis

In the first induction (Day 0), the hair on the skin in the back of anesthetized mice was removed using an electronic clipper, and the remaining hair was epilated using hair removal cream. One hundred (100) mg of HDM (*Dermatophagoides farinae*) ointment (Biostir, Japan) was administered topically to the skin in the shaved back. From the second induction, the skin bather function was disrupted by applying 150 μL 4% sodium dodecyl sulfate to the dorsal skin 2 hours prior to the HDM ointment administration. These procedures were repeated twice weekly. Several factors (erythema/hemorrhage and scar/dryness) were scored on Days 3, 6, 14, and 21 according to an evaluation criterion of 0 (none), 1 (mild), 2 (moderate) or 3 (severe) according to the manufacturer's instructions (Biostir). The sum of the scores was taken as overall dermatitis score.

(5) Establishment of RAW264.7 Transformant

Clec10a cDNA was made from C57BL/6J mice or NC/Nga mice and labeled with a sequence encoding a Flag tag and subcloned into a pMXs-IRES-GFP retroviral vector. A RAW264.7 transformant stably expressing C57BL/6J type or NC/Nga type Clec10a was established based on a routine method.

(6) ELISA Assay

Serum IgE antibodies were measured using capturing antibodies against mouse IgE (R35-72) and biotinylated anti-mouse IgE (R35-118) followed by HRP-labeled streptavidin (Ge Healthcare, RPN1231V). Purified mouse IgE (C38-2, BD Biosciences) was used as a standard. Serum IgG1 was measured using capturing antibodies against mouse IgG1 (A85-3) and HRP-labeled antibodies against mouse IgG1. Purified mouse IgG1 (107.3, BD Biosciences) was used as a standard. Serum IgG2c was detected by mouse ELISA Quantitation Set (Bethyl, E90-136).

(7) Preparation of Bone Marrow Macrophage (BMMP)

Bone marrow cells were cultured on a culture dish (Corning, 430166 or 430167) in an RPMI1640 complete medium containing 10% FBS in the presence of 10 ng/ml GM-CSF (Rd Systems) and 7 ng/mL IL-4 (Wako). On Day 2, 70% of non-adherent cells were removed and a fresh medium containing GM-CSF and IL-4 was added. On Day 5, 100% of non-adherent cells were removed by washing with PBS and a fresh medium containing GM-CSF and IL-4 was added. On Day 7, all non-adherent cells were removed by PBS wash and adherent cells were used in later experiments. For the analysis of cytokine secretion and Syk phosphorylation, CD115$^+$ BMMP was concentrated using anti CD115 antibodies (BioLegend) and anti-rat IgG microbeads (Miltenyi Biotec).

(8) Analysis of Cytokine Secretion

CD115$^+$BMMP was stimulated with 100 μg/mL HDM extract (*Dermatophagoides farinae*) (COSMO BIO), 1 ng/mL lipopolysaccharide, or 200 pg/mL Pam2CSK4 in the presence or absence of 0.5 μM TAK-242 (Merck) for 15 minutes. After 6-hour stimulation, culture supernatants were collected and the concentration of each cytokine was determined using cytometric bead array analysis (BD Biosciences).

(9) Synthesis of cDNA and Real-Time PCR (RT-PCR)

Total RNA was extracted from skin tissue or cells sorted by flow cytometry using Isogen reagent (Nippon Gene). Skin MP was sorted by CD45$^+$MHCII$^+$CD3$^-$CD19$^-$NK1.1$^-$Ly-6G$^-$EpCAM$^-$CD64$^+$and DC was sorted by CD45$^+$MHCII$^+$CD3$^-$CD19$^-$NK1.1$^-$Ly-6G$^-$EpCAM$^-$CD64$^-$). CD3$^+$CD4$^+$ cells were also obtained. cDNA was synthesized using High Capacity RNA-to-cDNA Kit (Applied Biosystems). Gene expression of Clec10a and inflammatory cytokines was measured by quantitative RT-PCR using SYBR Gree Master Mix (Applied Biosystems) and specific primers. An expression level of Gapdh was used as an internal reference for standardized data. The primer sequences used were as shown in Table 1 below.

TABLE 1

| Gene name | Forward | Reverse |
|---|---|---|
| Clec10a | 5'-ACCCAAGAGCCTGGTAAAGC-3' | 5'-GATCCAATCACGGAGACGAC-3' |
| Tnf | 5'-GGGCCACCACGCTCTTC-3' | 5'-GGTCTGGGCCATAGAACTGATG-3' |
| Il6 | 5'-GAGGATACCACTCCCAACAGACC-3' | 5'-AAGTGCATCATCGTTGTTCATACA-3' |
| Cxcl1 | 5'-ACTCAAGAATGGTCGCGAGG-3' | 5'-GTGCCATCAGAGCAGTCTGT-3' |
| Cxcl2 | 5'-AAGTTTGCCTTGACCCTGAA-3' | 5'-AGGCACATCAGGTACGATCC-3' |
| Ifng | 5'-ACAGCAAGGCGAAAAAGGATG-3' | 5'-TGGTGGACCACTCGGATGA-3' |
| Il4 | 5'-ATCATCGGCATTTTGAACGAGG-3' | 5'-TGCAGCTCCATGAGAACACTA-3' |
| Il17 | 5'-TTTAACTCCCTTGGCGCAAAA-3' | 5'-CTTTCCCTCCGCATTGACAC-3' |
| Il10 | 5'-GCTGGACAACATACTGCTAACC-3' | 5'-ATTTCCGATAAGGCTTGGCAA-3' |
| Tbx21 | 5'-AGCAAGGACGGCGAATGTT-3' | 5'-CGGTGGACATATAAGCGGTTC-3' |
| Gata3 | 5'-TTATCAAGCCCAAGCGAAGG-3' | 5'-CATTAGCGTTCCTCCTCCAGAG-3' |
| Rcrc | 5'-GGAGGACAGGGAGCCAAGTT-3' | 5'-CCGTAGTGGATCCCAGATGACT-3' |
| Foxp3 | 5'-CCCATCCCCAGGAGTCTTG-3' | 5'-ACCATGACTAGGGGCACTGTA-3' |
| Gapdh | 5'-TGGTGAAGGTCCGTGTGAAC-3' | 5'-ATGAAGGGGTCGTTGATGGC-3' |

(10) Retroviral Gene Transfer

Wild-type Clec10a cDNA was subcloned into a pMXs-puro retroviral vector (Cell Biolabs). To create site-specific Clec10a mutants, the PCR primers of the sense strands were designed so as to contain phenylalanine (TTC) instead of tyrosine (TAC). The resulting mutant cDNA was confirmed by sequencing. Retroviruses were obtained by transfecting 293GP packaging cells with wild-type or mutant Y3F cDNA or VSV-G expression vector pCMV-VSV-G. BMMP was infected with viral supernatants added with polybrene (8 μg/ml, Sigma-Aldrich) on Days 2 and 4. After centrifugation, the supernatants containing viruses were removed and the medium was replaced with a fresh BMMP medium. On Day 5, the medium was replaced with a fresh BMMP medium and non-adherent cells were removed by washing with PBS wash on Day 7 and adherent cells were used in the experiment.

(11) Preparation of Clec10a-Fc Chimera

A mouse Clec10a chimeric construct (Clec10a-Fc) was made by cloning the extracellular region of mouse Clec10a into a pME18S expression vector containing the Fc region of human IgG1. Clec10a-Fc was transfected into HEK293T cells using Lipofectamine 2000 (Thermo Fisher Scientific) and the medium was then replaced with GIT medium (KOHJIN BIO). Clec10a-Fc was purified from the culture supernatants using protein a agarose (Bio-Rad Laboratories).

(12) Isolation of Clec10a Ligand

An HDM extract dissolved in a buffer containing 150 mM NaCl, 50 mM Tris, 1 mM $CaCl_2$, and 0.01% Tween 20 was subjected to a pull-down assay using Clec10a-Fc. The ligand bound to Clec10a-Fc was eluted using 30 mM EDTA or 200 mM galactose. The eluate was dialyzed with a centrifugal filter unit (Merck, UFC503024) using PBS as an external fluid, named Clec10a-L, and used as one of Clec10a ligands.

(13) Alcian Blue Staining and Silver Staining

The Clec10a ligand was developed by SDS-PAGE. Immediately after electrophoresis, the gel was washed with deionized water and 10% acetate buffer (deionized water with 10% acetic acid and 30% ethanol) and stained for 2 hours at room temperature with or without an alcian blue solution (pH 2.5) (Wako, 013-13801) and then destained with 3% acetate buffer and 10% acetate buffer. The gel was silver-stained according to the manufacturer's instructions (Pierce Silver Stain Kit, Thermo Fisher Scientific).

(14) Fractionation of Clec10a Ligand

The Clec10a ligand was developed by SDS-PAGE and the gel was cut out in a manner of separating according to size. The cut gels were mechanically milled and incubated overnight in PBS with agitation. The supernatant was collected after centrifugation at 17400 g for 10 minutes and dialyzed with a centrifugal filter unit (Merck, UFC503024) using PBS as an external fluid.

(15) Immunoblotting

To analyze phosphorylation of Syk, BMMP was stimulated with an HDM extract (100 μg/mL) at 37° C. for 0, 10, or 30 minutes. The stimulated BMMP was lysed with a 1% NP-40 lysis buffer and separated by SDS-PAGE. It was transferred onto a PVDF membrane by electroblotting, immunoblotted with anti-phosphorylated Syk antibodies and anti-Syk antibodies, and detected using HRP-labeled anti-rabbit IgG antibodies.

To analyze tyrosine phosphorylation of Clec10a, BMMP was stimulated with an HDM extract (100 μg/mL) at 37° C. for 0 min, 10 min, or 30 min. The stimulated BMMP was lysed with a 1% NP-40 lysis buffer and subjected to Immunoprecipitation with anti-Clec10a mAb. An immune precipitate was developed by SDS-PAGE and transferred onto a PVDF membrane and immunoblotted with HRP-labeled anti-phosphorylated tyrosine antibodies or anti-Clec10a antibodies and BRP-labeled anti-rabbit IgG antibodies.

To analyze association of Clec10a with Syk or SHP-1, BMMP was pretreated in the presence or absence of 5 mM Syk inhibitor IV (Merck, 574714) at 37° C. for 30 minutes and stimulated with an HDM extract (100 μg/mL) at 37° C. for 0 min, 10 min, or 30 min. BMMP was lysed with a 0.2% digitonin buffer and immunoprecipitated with anti-Clec10a mAb. An immune precipitate was transferred onto a PVDF membrane as described above and immunoblotted using anti-Syk antibodies, anti-SHP-1 antibodies, or anti-Clec10a antibodies, and then detected with HRP-labeled anti-rabbit IgG antibodies or goat IgG antibodies. All proteins were detected using enhanced chemiluminescence (Thermo Fisher Scientific).

After pretreatment at 37° C. for 16 hours in the presence or absence of peptide N-glycosidase F (PNGase F PRIM™, NZS1, N-Zyme Scientific) and thermal metamorphism at 95° C. for 5 minutes, a Clec10a ligand was pretreated at 40° C. for 16 hours in the presence or absence of 0.05 M NaOH, separated by SDS-PAGE, transferred into a PVDF membrane, and immunoblotted with biotinylated Clec10a-Fc and HRP-labeled streptavidin.

(16) Establishment and Stimulation of Reporter Cell

The intracellular region of human CD3ζ was obtained from a vector provided by LL Lanier (University of California, San Francisco). The extracellular region of mouse or human Clec10a or the extracellular region of human Asgr1 was subcloned into a pMXs-puro retroviral vector. 2B4-NFAT-GFP reporter cells were provided from H. Arase (University of Osaka). 2B4-NFAT-GFP reporter cells stably expressing mouse or human Clec10a were made as described previously. The reporter cells were incubated for 18 hours in the presence or absence of anti-Clec10a mAb, Lewis X (GlycoTech), Lewes Y (GlycoTech), galactose (Sigma-Aldrich), glucose (Sigma-Aldrich) or mannose (Sigma-Aldrich). The reporter cells were also cultured on a galactosidase (R & D Systems, 5704 GH or 5549 GH) or glucosidase (R & D Systems, 8329-GH), or Clec10 ligand-coated plate, or an HDM extract-coated plate treated with size-fractionated Clec10a ligand or untreated. Activation of NFAT-GFP was monitored by flow cytometry.

(17) Lectin Microarray Analysis

Lectin microarrays were made using a non-contact microarray printing robot (MicroSys4000; Genomic Solutions) according to the previous method. Samples were fluorescently labeled with Cy3 Mono-Reactive dye (Ge) and excess Cy3 was removed using a Sephadex g-25 desalting column (Ge). After 10 fold dilution with a probe solution (25 mM Tris-HCl, pH 7.5, 140 mM NaCl) (TBS) containing 2.7 mM KCl, 1 mM $CaCl_2$, 1 mM $MnCl_2$, and 1% Triton X-100, a Cy3-labeled sample was applied to a lectin microarray and incubated at 20° C. overnight. The sample was washed with a probe solution, and a fluorescence image was obtained using an evanescent-field activated fluorescence scanner (Bio-Rad scan 200, Rexxam Co. Ltd.). Lectin signals in triplicate spots were averaged for each protein sample and normalized to an average value of 96 lectins. The list of lectins was as shown in Table 2.

TABLE 2

| | Name | Species | Origin | Source2 | Rough specificity1 |
|---|---|---|---|---|---|
| 1 | LFA | *Limax flavus* | Natural | EY Lab. | Sia |
| 2 | WGA | *Triticum vulgaris* | Natural | EY Lab. | (GlcNAc)n, polySia |
| 3 | PVL | *Psathyrella velutina* | Natural | Wako | Sia, GlcNAc |
| 4 | MAL | *Maackia amurensis* | Natural | Seikagaku | α2-3Sia |
| 5 | MAH | *Maackia amurensis* | Natural | Vector | α2-3Sia |
| 6 | ACG | *Agrocybe cylindracea* | Natural | JOM | α2-3Sia |
| 7 | rACG | *Agrocybe cylindracea* | *E.coli* | AIST | α2-3Sia |
| 8 | rGal8N | *Homo sapiens* | *E.coli* | AIST | α2-3Sia |
| 9 | SNA | *Sambucus nigra* | Natural | Seikagaku | α2-6Sia |
| 10 | SSA | *Sambucus sieboldiana* | Natural | Vector | α2-6Sia |
| 11 | TJAI | *Trichosanthes japonica* | Natural | Vector | α2-6Sia |
| 12 | rPSL1a | *Polyporus squamosus* | *E.coli* | AIST | α2-6Sia |
| 13 | PHAL | *Phaseolus vulgaris* | Natural | Seikagaku | GlcNAcβ1-6Man (Tetraantenna) |
| 14 | DSA | *Datura stramonium* | Natural | Seikagaku | GlcNAcβ1-6Man (Tetraantenna) |
| 15 | TxLcl | *Tulipa gesneriana* | Natural | JOM | Galactosylated N-glycans up to triantenna |
| 16 | ECA | *Erythrina cristagalli* | Natural | Seikagaku | βGal |
| 17 | RCA120 | *Ricinus communis* | Natural | Vector | βGal |
| 18 | rGal7 | *Homo sapiens* | *E.coli* | AIST | Type1 LacNAc, chondroitin polymer |
| 19 | rGal9N | *Homo sapiens* | *E.coli* | AIST | GalNAcα1-4Gal (A), PolyLacNAc |
| 20 | rGal9C | *Homo sapiens* | *E.coli* | AIST | PolyLacNAc, Branched LacNAc |
| 21 | rC14 | *Gallus gallus domesticus* | *E.coli* | AIST | Branched LacNAc |
| 22 | rDiscoidinII | *Dictyostelium dicodeum* | *E.coli* | AIST | LacNAc, Galβ1-3GalNAc (T), GalNAc (Tn) |
| 23 | BPL | *Bauhinia purpurea alba* | Natural | Vector | Galβ1-3GlcNAc(GalNAc), α/β GalNAc |
| 24 | rCGL2 | *Homo sapiens* | *E.coli* | AIST | GalNAcα1-3Gal (A), PolyLacNAc |
| 25 | PHAE | *Phaseolus vulgaris* | Natural | Vector | bisecting GlcNAc |
| 26 | GSLII | *Griffonia simplicifolia* | Natural | Vector | GlcNAcβ1-4Man |
| 27 | rSRL | *Sclerotium rolfsii* | *E.coli* | AIST | Core1,3, agalacto N-glycan |
| 28 | UDA | *Urtica dioica* | Natural | Vector | (GlcNAc)n |
| 29 | PWM | *Phytolacca americana* | Natural | Vector | (GlcNAc)n |
| 30 | rF17AG | *Escherichia coli* | *E.coli* | AIST | GlcNAc |
| 31 | rGRFT | *Griffithia* sp. | *E.coli* | AIST | Man |
| 32 | NPA | *Narcissus pseudonarcissus* | Natural | Seikagaku | Manα1-3Man |
| 33 | ConA | *Canavalia ensiformis* | Natural | Vector | M3, Manα1-2Manα1-3(Manα1-6)Man, GlcNAcβ1-2Manα1-3(Manα 1-6)Man |
| 34 | GNA | *Galanthus nivalis* | Natural | Vector | Manα 1-3Man, Manα 1-6Man |
| 35 | HHL | *Hippeastrum hybrid* | Natural | Vector | Manα 1-3Man, Manα 1-6Man |
| 36 | ASA | *Allium sativum* | Natural | JOM | Galβ 1-4GlcNAcβ1-2Man |
| 37 | DBAI | *Dioscorea batatas* | Natural | JOM | High-man |
| 38 | CCA | *Castanea crenata* | Natural | JOM | Galactosylated N-glycans up to triantenna |
| 39 | Heltuba | *Helianthus tuberosus* | Natural | JOM | Manα 1-3Man |
| 40 | rHeltuba | *Helianthus tuberosus* | *E.coli* | AIST | Manα 1-3Man |
| 41 | ADA | *Allomyrina dichtoma* | Natural | JOM | α2-6Sia, Forssman, A, B |
| 42 | VVAII | *Vicia villosa* | Natural | JOM | Man, Agalacto |
| 43 | rOrysata | *Oryza sativa* | *E.coli* | AIST | Manα 1-3Man, Highman, biantenna |
| 44 | rPALa | *Phlebodium aureum* | *E.coli* | AIST | Man5, biantenna |
| 45 | rBanana | *Musa acuminata* | *E.coli* | AIST | Manα 1-2Manα 1-3(6)Man |
| 46 | rCalsepa | *Calystegia sepium* | *E.coli* | AIST | Biantenna with bisecting GlcNAc |
| 47 | rRSL | *Ralstonia solanacearum* | *E.coli* | AIST | αMan,α1-2Fuc (H), α1-3Fuc (Lex), α1-4Fuc (Lea) |
| 48 | rBC2LA | *Burkholderia cenocepacia* | *E.coli* | AIST | αMan, High-man |
| 49 | AOL | *Aspergillus oryzae* | Natural | Vector | α1-2Fuc (H), α1-3Fuc (Lex), α1-3Fuc (Lea) |
| 50 | AAL | *Aleuria aurantia* | Natural | Vector | α1-2Fuc (H), α1-3Fuc (Lex), α1-4Fuc (Lea) |
| 51 | rAAL | *Aleuria aurantia* | *E.coli* | AIST | α1-2Fuc (H), α1-3Fuc (Lex), |

TABLE 2-continued

| | | Lectin used in lectin microarray | | | |
|---|---|---|---|---|---|
| | Name | Species | Origin | Source2 | Rough specificity1 |
| 52 | rPAIIL | *Pseudomonas aeruginosa* | *E.coli* | AIST | α1-3Fuc (Lea)<br>αMan, α1-2Fuc (H),<br>α1-3Fuc (Lex),<br>α1-4Fuc (Lea) |
| 53 | rRSIIL | *Ralstonia solanacearum* | *E.coli* | AIST | α1-2Fuc (H),<br>α1-3Fuc (Lex),<br>α1-3Fuc (Lea) |
| 54 | rPTL | *Pholiota terrestris* | *E.coli* | AIST | α1-6Fuc |
| 55 | PSA | *Pisum sativum* | Natural | Seikagaku | α1-6Fuc up to biantenna |
| 56 | LCA | *Lens culinaris* | Natural | Vector | α1-6Fuc up to biantenna |
| 57 | rAOL | *Aspergillus oryzae* | *E.coli* | AIST | α1-2Fuc (H),<br>α1-3Fuc (Lex),<br>α1-3Fuc (Lea) |
| 58 | rBC2LCN | *Burkholderia cenocepacia* | *E.coli* | AIST | Fuc α1-2Galβ1-3GlcNAc<br>(GalNAc) |
| 59 | LTL | *Lotus tetragonolobus* | Natural | Seikagaku | Lex, Ley |
| 60 | UEAI | *Ulex europaeus* | Natural | Vector | α1-2Fuc |
| 61 | TJAII | *Trichosanthes japonica* | Natural | Vector | α1-2Fuc |
| 62 | MCA | *Momordica charantia* | Natural | JOM | α1-2Fuc |
| 63 | GSLI | *Griffonia simplicifolia* | Natural | Seikagaku | αGalNAc (A, Tn), αGal (B) |
| 64 | PTLI | *Psophocarpus tetragonolobus* | Natural | Tokyo Kasei | αGalNAc (A, Tn) |
| 65 | GSLIA4 | *Griffonia simplicifolia* | Natural | EY Lab. | αGalNAc (A, Tn) |
| 66 | rGC2 | *Geodia cydonium* | *E.coli* | AIST | α1-2Fuc (H),<br>αGalNAc (A),<br>αGal (B) |
| 67 | GSLIB4 | *Griffonia simplicifolia* | Natural | Vector | αGal (B) |
| 68 | rMOA | *Marasmius oreades* | *E.coli* | AIST | αGal (B) |
| 69 | EEL | *Euonymus europaeus* | Natural | Vector | αGal (B) |
| 70 | rPAIL | *Pseudomonas aeruginosa* | *E.coli* | AIST | α,βGal, αGalNAc (Tn) |
| 71 | LEL | *Lycopersicon esculentum* | Natural | Vector | Polylactosamine, (GlcNAc)n |
| 72 | STL | *Solanum tuberosum* | Natural | Seikagaku | Polylactosamine, (GlcNAc)n |
| 73 | rGal3C | *Homo sapiens* | *E.coli* | AIST | LacNAc, polylactosamine |
| 74 | rLSLN | *Laetiporus sulphureus* | *E.coli* | AIST | LacNAc, polylactosamine |
| 75 | rCGL3 | *Coprinopsis cinerea* | *E.coli* | AIST | LacDiNAc |
| 76 | PNA | *Arachis hypogaea* | Natural | Vector | Galβ 1-3GalNAc (T) |
| 77 | ACA | *Amaranthus caudatus* | Natural | Vector | Galβ 1-3GalNAc (T) |
| 78 | HEA | *Hericium erinaceum* | Natural | JOM | Galβ 1-3GalNAc (T) |
| 79 | ABA | *Agarics bisporuserinaceum* | Natural | Vector | Galβ 1-3GalNAc (T),<br>GlcNAc |
| 80 | Jacalin | *Artocarpus integrifolia* | Natural | Seikagaku | Galβ 1-3GalNAc (T),<br>GalNAcα(Tn) |
| 81 | MPA | *Maclura pomifera* | Natural | Seikagaku | Galβ 1-3GalNAc (T),<br>GalNAcα(Tn) |
| 82 | HPA | *Helix pomatia* | Natural | Seikagaku | αGalNAc (A, Tn) |
| 83 | VVA | *Vicia villosa* | Natural | Vector | α, βGalNAc<br>(A, Tn, LacDiNAc) |
| 84 | DBA | *Dolichos biflorus* | Natural | Vector | α, BGalNAc<br>(A, Tn, LacDiNAc) |
| 85 | SBA | *Glycine max* | Natural | EY Lab. | α, βGalNAc<br>(A, Tn, LacDiNAc) |
| 86 | rPPL | *Pleurocybella porrigens* | *E.coli* | AIST | α, βGalNAc<br>(A, Tn, LacDiNAc) |
| 87 | rCNL | *Clitocybe nebularis* | *E.coli* | AIST | α, BGalNAc<br>(A, Tn, LacDiNAc) |
| 88 | rXCL | *Xerocomus chrysenteron* | *E.coli* | AIST | Core1,3,<br>agalacto N-glycan |
| 89 | VVA! | *Vicia villosa* | Natural | JOM | GalNAcβ1-3(4)Gal |
| 90 | WFA | *Wisteria floribunda* | Natural | Vector | Terminal GalNAc,<br>LacDiNAc |
| 91 | rABA | *Agarics bisporus* | *E.coli* | AIST | Galβ1-3GalNAc (T),<br>GlcNAc |
| 92 | rDiscoidinI | *Dictyostelium Discodeum* | *E.coli* | AIST | Gal |
| 93 | DBAIII | *Dioscorea batatas* | Natural | JOM | Maltose |
| 94 | rMalectin | *Homo sapiens* | *E.coli* | AIST | Glcα1-2Glc |
| 95 | CSA | *Oncorhynchus keta* | Natural | JOM | Rhamnose, Galα1-4Gal |
| 96 | FLAG-EW29Ch-E20K | *Lumbricus terrestris* | *E.coli* | AIST | 6-sulfo-Gal |

Abbreviations:

Gal (D-galactose), GalNAc (N-acetyl-galactosamine), GlcNAc (N-acetyl-glucosamine), Fuc (L-fucose), Sia (Sialic acid), and LacNAc (N-acetyl-lactosamine).
[2]Specific data was obtained by frontal affinity chromatography and sugar conjugate microarrays.
[3]Abbreviations: JOM (J-OIL MILLS, INC), Vector (VECTOR LABORATORIES), Seikagaku (SEIKAGAKU CORPORATION), EY (EY LABORATORIES, INC), and AIST (National Institute of Advanced Industrial Science and Technology)

(18) Sugar Conjugate Microarray Analysis

A sugar conjugate microarray containing 98 sugar conjugates (Table 3) was prepared according to a known method using a non-contact microarray printing robot (MicroSys 4000; Genomic Solutions). Clec10a-Fc (10 µg/mL) was pre-complexed with Cy3-labeled goat anti-human IgG, Fc (Jackson, 109-165-098) (1 µg/mL) in advance and incubated with sugar conjugate microarrays (80 µL/well) overnight at 20° C.

TABLE 3

| Glycan used in sugar conjugate microarray | | | | |
|---|---|---|---|---|
| Trivial name | Presentation | Glycans | Source | Cat# |
| αFuc | PAA | Fucα 1-PAA | Glycotech | 01-007 |
| Fucα2Gal | PAA | Fucα 1-2Galβ 1-PAA | Glycotech | 01-019 |
| Fucα3GlcNAc | PAA | Fucα 1-3GlcNAcβ 1-PAA | Glycotech | 01-024 |
| Fucα4GlcNAc | PAA | Fucα 1-4GlcNAcβ 1-PAA | Glycotech | 01-025 |
| H type1 | PAA | Fucα 1-2Galβ 1-3GlcNAcβ 1-PAA | Glycotech | 01-037 |
| H type2 | PAA | Fucα 1-2Galβ 1-4GlcNAcβ 1-PAA | Glycotech | 08-034 |
| H type3 | PAA | Fucβ 1-2Galβ 1-3GalNAcα 1-PAA | Glycotech | 08-060 |
| A | PAA | GalNAc 1-3(Fucα 1-2)Galβ 1-4GlcNAcβ 1-PAA | Glycotech | 08-091 |
| B | PAA | Galα 1-3(Fucα 1-2)Galβ 1-4GlcNAcβ 1-PAA | Glycotech | 08-092 |
| Le$^a$ | PAA | Galβ 1-3(Fucα 1-4)GlcNAcβ 1-PAA | Glycotech | 01-035 |
| [3S]Le$^a$ | PAA | (3OSO3)Galβ 1-3(Fucα 1-4)GlcNAcβ 1-PAA | Glycotech | 01-040 |
| Le$^b$ | PAA | Fucα 1-2Galβ 1-3(Fucα 1-4)GlcNAcβ 1-PAA | Glycotech | 08-042 |
| Le$^x$ | PAA | Galβ.1-4(Fucα 1-3)GlcNAcβ 1-PAA | Glycotech | 01-036 |
| Le$^y$ | PAA | Fucα 1-2Galβ1-4(Fucα 1-3)GlcNAcβ 1-PAA | Glycotech | 08-043 |
| α Neu5Ac | PAA | Neu5Acα 2-PAA | Glycotech | 01-012 |
| α Neu5Gc | PAA | Neu5Gcα 2-PAA | Glycotech | 01-051 |
| Sia2 | PAA | Neu5Acα 2-8Neu5Acα 2-PAA | Glycotech | 08-064 |
| Sia3 | PAA | Neu5Acα 2-8Neu5Acα 2-8Neu5Acα 2-PAA | Glycotech | 01-081 |
| 3'SiaLec | PAA | Neu5Acα 2-3Galβ 1-3GlcNAcβ 1-PAA | Glycotech | 01-078 |
| 3'SL | PAA | Neu5Acα 2-3Galβ 1-4Glcβ 1-PAA | Glycotech | 01-038 |
| 3'SLN | PAA | Neu5Acα 2-3Galβ 1-4GlcNAcB 1-PAA | Glycotech | 01-077 |
| sLe$^a$ | PAA | Neu5Acα 2-3Galβ 1-3(Fucα 1-4)GlcNAcββ 1-PAA | Glycotech | 08-044 |
| sLe$^x$ | PAA | Neu5Acα 2-3Galβ 1-4(Fucα 1-3)GlcNAcp 1-PAA | Glycotech | 01-045 |
| 6'SL | PAA | Neu5Acα 2-6Galβ 1-4Glcβ 1-PAA | Glycotech | 01-039 |
| β Gal | PAA | Galβ 1-PAA | Glycotech | 01-004 |
| [3S] β Gal | PAA | (3OSO3)Galβ 1-PAA | Glycotech | 01-015 |
| A-di | PAA | GalNAcα 1-3Galβ 1-PAA | Glycotech | 01-017 |
| Lac | PAA | Galβ 1-4Glcβ 1-PAA | Glycotech | 01-021 |
| Le$^c$ | PAA | Galβ 1-3GlcNAcβ 1-PAA | Glycotech | 01-020 |
| [3'S]Le$^c$ | PAA | (3OSO3)Galβ 1-3GlcNAcβ 1-PAA | Glycotech | 01-062 |
| LN | PAA | Galβ 1-4GlcNAcβ 1-PAA | Glycotech | 01-022 |
| [3'S]LN | PAA | (3OSO3)Galβ 1-4GlcNAcβ 1-PAA | Glycotech | 01-061 |
| [6S]LN | PAA | Galβ 1-4(6OSO3)GlcNAcβ 1-PAA | Glycotech | 01-066 |
| [6'S]LN | PAA | (6OSO3)Galβ 1-4GlcNAcβ 1-PAA | Glycotech | 01-068 |
| β GalNAc | PAA | GalNAcβ 1-PAA | Glycotech | 01-011 |
| di-GalNAcβ | PAA | GalNAcβ 1-3GalNAcβ 1-PAA | Glycotech | 01-070 |
| LDN | PAA | GalNAcβ 1-4GlcNAcβ 1-PAA | Glycotech | 01-057 |
| GA2 | PAA | GalNAcβ 1-4Gal 1-4Glcβ 1-PAA | Glycotech | 08-074 |
| BGlcNAc | PAA | GlcNAcβ 1-PAA | Glycotech | 01-009 |
| [6S]β GlcNAc | PAA | (6OSO3)GlcNAcβ 1-PAA | Glycotech | 01-016 |
| α Man | PAA | Manα 1-PAA | Glycotech | 01-005 |
| βMan | PAA | Manβ 1-PAA | Glycotech | 01-050 |
| [6P]Man | PAA | (6OPO4)Manα 1-PAA | Glycotech | 01-006 |
| Tn | PAA | GalNAcα 1-PAA | Glycotech | 01-010 |
| Core1 | PAA | Galβ 1-3GalNAcα 1-PAA | Glycotech | 08-023 |
| Core2 | PAA | Galβ 1-3(GlcNAcβ 1-6)GalNAcα 1-PAA | Glycotech | 01-083 |
| Core3 | PAA | GlcNAcβ 1-3GalNAcα 1-PAA | Glycotech | 01-071 |
| Core4 | PAA | GlcNAcβ 1-3(GlcNAcβ 1-6)GalNAcα 1-PAA | Glycotech | 01-089 |
| Forssman | PAA | GalNAcα 1-3GalNAcβ 1-PAA | Glycotech | 01-026 |
| Core6 | PAA | GlcNAcβ 1-6GalNAcα 1-PAA | Glycotech | 01-072 |

TABLE 3-continued

| Glycan used in sugar conjugate microarray | | | | |
|---|---|---|---|---|
| Trivial name | Presentation | Glycans | Source | Cat# |
| Core8 | PAA | Galα 1-3GalNAcα 1-PAA | Glycotech | 01-028 |
| [3'S]Core1 | PAA | (3OSO3)Galβ 1-3GalNAcα 1-PAA | Glycotech | 08-069 |
| Galβ-Core3 | PAA | Galβ 1-4GlcNAcβ 1-3GalNAcα 1-PAA | Glycotech | 01-116 |
| STn | PAA | Neu5Acα 2-6GalNAcα 1-PAA | Glycotech | 01-059 |
| STn (Gc) | PAA | Neu5Gcα 2-6GalNAcα 1-PAA | Glycotech | 01-107 |
| ST | PAA | Neu5Acα 2-3Galβ 1-3GalNAcα 1-PAA | Glycotech | 01-088 |
| Siaa 2-6Core1 | PAA | Galβ 1-3(Neu5Acα 2-6) GalNAcα 1-PAA | Glycotech | 01-113 |
| α Gal | PAA | Galα 1-PAA | Glycotech | 01-003 |
| Galα 1-2Gal | PAA | Galα 1-2Galβ 1-PAA | Glycotech | 01-056 |
| Gaα 1-3Gal | PAA | Galα 1-3Galβ 1-PAA | Glycotech | 01-018 |
| Galα 1-3Lac | PAA | Galα 1-3Galβ 1-4Glcβ 1-PAA | Glycotech | 01-075 |
| Galα 1-3LN | PAA | Galα 1-3Galβ 1-4GlcNAcβ 1-PAA | Glycotech | 01-079 |
| Galα 1-4LN | PAA | Galα 1-4Galβ 1-4GlcNAcB 1-PAA | Glycotech | 01-110 |
| Melibiose | PAA | Galα 1-6Glcβ 1-PAA | Glycotech | 01-063 |
| α Glc | PAA | Glcα 1-PAA | Glycotech | 01-001 |
| β Glc | PAA | Glcβ 1-PAA | Glycotech | 01-002 |
| Maltose | PAA | Glcα 1-4Glcβ 1-PAA | Glycotech | 01-054 |
| α Rha | PAA | Rhamnosea 1-PAA | Glycotech | 01-008 |
| Chitobiose | PAA | GlcNAcβ 1-4GlcNAcβ 1-PAA | Glycotech | 08-057 |
| Negative PAA | PAA | — | Glycotech | 01-000 |

(19) Knock Down of Human Asgr1

CD14+ monocytes were concentrated from peripheral blood mononuclear cells using anti CD14 microbeads (Miltenyi Biotec, 130-050-201) and cultured in the presence of GM-CSF for 2 days. The monocytes were treated with siRNA specific for ASGR1 (SMARTpool Accell siRNA, Dharmacon) or a mixture of control siRNA and siRNA delivery agents. The monocytes were then stimulated with 100 μg/mL HDM extract for 6 hours. Concentrations of various cytokines in culture supernatants were determined using cytometric bead array analysis (BD Biosciences).

(20) Human Skin Gene Expression Data

Published microarray data (GSE5667) was used to analyze the expression of human ASGR1 in the pathologic state of human skin and atopic dermatitis.

(21) Statistical Analysis

Statistical analysis was performed using two-sided Student's t-test (GraphPad Prism 5), post-hoc Tukey-Kramer test and ANOVA test (GraphPad Prism 5), or Pearson correlation test (two-sided, GraphPad Prism 5).

Example 1 Exome Analysis of Atopic Dermatitis Model Mouse

In this example, exome analysis of NC/Nga mice as model mice of atopic dermatitis was performed to identify causative genes of atopic dermatitis.

The NC/Nga mice were purchased from Charles River, Japan. DNA was extracted from blood from the NC/Nga mice under conditions suitable for extraction of mouse DNA using QIAamp DNA blood Mini Kit (Qiagen, Venlo, Netherlands). The exome analysis of the resulting DNA was performed as follows. DNA libraries were obtained using SureSelect Library prep kit (post-pool version 4; Agilent Technologies, Santa Clara, CA) and SureSelect Mouse All Exon Kit (Agilent Technologies) according to the manufacturer's manual. The resulting DNA libraries were subjected to emulsion PCR (SOLiD EZ Bead Emulsifier kit; Thermo Fisher Scientific, Waltham, MA) to generate clonal DNA fragments on beads, which were then subjected to bead enrichment (SOLiD EZ Bead Enrichment kit; Thermo Fisher Scientific, Waltham, MA). The resulting beads were sequenced on a SOLiD 5500xl sequencer as single end 60-bp reads. The resulting read were aligned with the mouse reference genome (NCBI37/mm9) using LifeScope version 2.5.1 (Life Sciences) to obtain a BAM file. Variant calls were performed using SAMtool according to the protocol described in Genome Analysis Toolkit, Picard (http://broadinstitute.github.io/picard), and only reads mapped to unique locations on the reference genome were used for analysis. Mutations were annotated using the ANNOVER software. Genetic variation in inbred mice other than NC/Nga was obtained from Release REL-1211 numbered according to the NCBIm 37 assembly (http://www.sanger-.ac.uk/science/data/mouse-genomes-project) and Mouse Genome Informatics website (http://www.informatics.jax-.org/). Sequencing was performed on an ABI 3130xl Genetic Analyzer (Thermo Fisher Scientific) using BigDye Terminator v1.1 Cycle Sequencing Kit (Thermo Fisher Scientific). The primers used were as shown in Table 4.

TABLE 4

| Primer used for confirmation of nonsense mutation or frameshift mutation in NC/Nga mouse by Sanger sequencing | | |
|---|---|---|
| Gene | | Primer sequence |
| Cdh20 | Forward | TCGGACTCAGAGCAGAGCTT |
|  | Reverse | CTCTGCTGGGTOCACTCACT |
| Tlr5 | Forward | GCCATTCTTCCTTGAACCAC |
|  | Reverse | ATGGCCGTGTGGGAGTATAA |

TABLE 4-continued

Primer used for confirmation of nonsense mutation or frameshift
mutation in NC/Nga mouse by Sanger sequencing

| Gene | | Primer sequence |
|------|---------|-----------------|
| Tmem141 | Forward | GATCAGGGACTCCAAAACCA |
| | Reverse | TGCTGAGGTAGGAGGGACTG |
| Qsox2 | Forward | AGACTCAGCCACGTGAACCT |
| | Reverse | TCGGGCTCAGACATTTCACT |
| Hc | Forward | TCGTGTTTTTAAATATTTTGCTTCC |
| | Reverse | CCCCACCCTCTTCTGGTACT |
| Tdpoz2 | Forward | GGTGGAAGTCAATGGTGGAG |
| | Reverse | TTGTCTCTGGGACTCAAAGGA |
| Gm572 | Forward | GTTTCGGCGCTTTTGTTTTA |
| | Reverse | CTTCAGAGGCCAGGACAAAG |
| Cyp3a57 | Forward | TGATGTTCTTCTTTGACCTTCC |
| | Reverse | TCCCTCTCTGAGTACCATCCA |
| Try4 | Forward | GAGGGCTCCACCTAACAACA |
| | Reverse | GTACAGACAGGGCCCATCAC |
| Klri2 | Forward | TGATGAGCACTCATTTCACACA |
| | Reverse | TCCCAGTGCCAACAGTTACA |
| Kira7 | Forward | AAAGTTAAAGAGTTGCCCCTTG |
| | Reverse | TGAATTATTGCAGGAAACAAATG |
| Ttc23 | Forward | GAACTGCTCTAACGCTGTGG |
| | Reverse | ACAGTGCCATCCAGGGTTC |
| Olfml1 | Forward | GGGCATTCATGGAAGATAGC |
| | Reverse | CATCCACAGCAAGGTCAATG |
| Foxr1 | Forward | CGCAGTTTCCCCTTCTCAT |
| | Reverse | TGGAGGTACAAGGTTCTGTGC |
| Cilp | Forward | AAGAGCAATGTGGGAGTTGC |
| | Reverse | AGCATCATGAGGCAGAGACA |
| Slc22a21 | Forward | GCTTGTTTTGCAACTGATGG |
| | Reverse | AGCACTGTTGTCGGTCACTG |
| Clec10a | Forward | TGAGGGAGAGGTAACCATGC |
| | Reverse | GGGCAAATGTACAGCACACA |
| Serpina3i | Forward | GCTGTCAGGACTCAGCAGTG |
| | Reverse | GGTCAGGGAGAATGAACAGG |
| Zkscan4 | Forward | AATCCACACGGGTGAGAAAC |
| | Reverse | CAGTGTGTATTGGCCACACC |
| Zfp957 | Forward | TGCAGAGCAAAGTCAAGGTT |
| | Reverse | CTTAGCGGCTGCGTTTTT |
| Timm8a2 | Forward | CATCCACCACATGACAGAGC |
| | Reverse | GTCCATTTCCCCACCTACCT |
| Pdzd2 | Forward | ATGCATGCTCGCTTTTTCTT |
| | Reverse | GAGGGATGGGGGAAGAGTTA |
| Cyp2d11 | Forward | AGGCAGAGTCCAACAGGAAA |
| | Reverse | CCTACCTTGGTGACGAGGAA |
| Kcnk7 | Forward | CCCCAGCCTCAGTATCAGAA |
| | Reverse | ATTTAGCCCAGAGTCGCTTG |

In the exon region of the genome of the NC/Nga mice, 70772 mutations were identified relative to the reference genome. The mutations with low quality values obtained from the GATK output were removed and 64518 mutations were obtained. Loss of function mutations, including nonsense mutation and frameshift mutation, were selected using the ANNOVER software. Thirty five (35) nonsense mutations and 48 frameshift mutations (induction of stop codons) were then identified. For each of these 83 genes, 46 mutations in 43 genes were selected for further sequence validation.

Of the 46 mutations, 24 mutations were confirmed by sequencing. The results were as shown in Table 5.

TABLE 5

| | | | | | | | | | |
|---|---|---|---|---|---|---|---|---|---|
| | Nonsense mutation and frameshift mutation in NC/Nga mouse confirmed by Sanger sequencing |
| Gene | Chromosome | Start | End | Function | Last exon2 | RefSeq number | Nucleotide substitution | Amino acid substitution | |
| Cdh20[1] | 1 | 106890959 | 106890959 | stopgain SNV | yes | NM_011800 | c.G2403A | p.W801X | |
| Tlr5 | 1 | 184902583 | 184902584 | frameshift substitution | no | NM_016928 | c.18_19delinsT | | |
| Tmem141 | 2 | 25476035 | 25476038 | frameshift deletion | yes | NM_001109993 | c.603_606del | | |
| Qsox2 | 2 | 26065186 | 26065186 | frameshift deletion | yes | NM_153559 | c.1845delC | | |
| Hc | 2 | 34898728 | 34898729 | frameshift deletion | no | NM_010406 | c.646_647del | | |
| Tdpoz2 | 3 | 93455535 | 93455535 | frameshift insertion | no | NM_001007222 | c.1051_1052insAG | | |
| Gm572 | 4 | 148045509 | 148045515 | frameshift deletion | yes | NM_001085505 | c.1172_1178del | | |
| Cyp3a57 | 5 | 146138201 | 146138205 | frameshift deletion | no | NM_001100180 | c.957_961del | | |
| Try4[1] | 6 | 41253356 | 41253356 | frameshift deletion | no | NM_011646 | c.114delG | | |
| Klri2[1] | 6 | 129683766 | 129683766 | stopgain SNV | no | NM_177155 | c.G407A | p.W136X | |
| Klra7[1] | 6 | 130169025 | 130169029 | frameshift deletion | yes | NM_014194 | c.693_697del | | |
| Ttc23[1] | 7 | 74837804 | 74837804 | frameshift deletion | no | NM_025905 | c.783delT | | |
| Olfml1 | 7 | 114733919 | 114733919 | frameshift deletion | yes | NM_172907 | c.676delT | | |
| Foxr1 | 9 | 44243294 | 44243294 | frameshift insertion | yes | NM_001033469 | c.638_639insAA | | |
| Cilp | 9 | 65127938 | 65127938 | frameshift deletion | yes | NM_173385 | c.3507delG | | |
| Slc22a21 | 11 | 53764775 | 53764775 | frameshift insertion | yes | NM_019723 | c.1678_1679insC | | |
| Clec10a[1] | 11 | 69983716 | 69983716 | stopgain SNV | no | NM_010796.2 | c.C706T | p.Q236X | |
| Serpina3i | 12 | 105504794 | 105504794 | frameshift deletion | no | NM_001199940 | c.747delC | | |
| Zkscan4 | 13 | 21576578 | 21576578 | frameshift insertion | yes | NM_001039115 | c.1416_1417insA | | |
| Zfp957 | 14 | 79613286 | 79613286 | frameshift insertion | yes | NM_001033215 | c.879_880insG | | |
| Timm8a2 | 14 | 122434145 | 122434154 | frameshift deletion | no | NM_001037744 | c.237_246del | | |
| Pdzd2[1] | 15 | 12375345 | 12375345 | stopgain SNV | no | NM_001081064.1 | c.C1054T | p.R352X | |
| Cyp2d11 | 15 | 82220453 | 82220453 | frameshift substitution | no | NM_001104531 | c.1156_1156delinsCACCC | | |
| Kcnk7 | 19 | 5706988 | 5706988 | frameshift insertion | yes | NM_010609 | c.1004_1005insT | | |

| Gene | rs number | human homolog | Other mouse strains |
|---|---|---|---|
| Cdh20[1] | | + | |
| Tlr5 | | + | MSM/Ms, JF1/Ms |
| Tmem141 | | + | MSM/Ms, JF1/Ms |
| Qsox2 | rs260851851 | + | NZO/HILtJ, PWK/PhJ |
| Hc | rs241579076 | + | A/J, AKR/J, DBA/2J, FVB/NJ, NOD/ShiLtJ |
| Tdpoz2 | | − | MSM/Ms, JF1/Ms |
| Gm572 | rs258174385 | + | 129S1/SvlmJ, A/J, AKR/J, BALB/cJ, C3H/HeJ, CAST/EiJ, CBA/J, NOD/ShiLtJ, PWK/PhJ, WSB/EiJ |
| Cyp3a57 | rs242224866 | + | 129S1/SvlmJ, AKR/J, CBA/J, LP/J, NZO/HILtJ |
| Try4[1] | | + | |
| Klri2[1] | | − | |
| Klra7[1] | | − | |
| Ttc23[1] | | + | |
| Olfml1 | rs262610229 | + | 129S1/SvlmJ, C3H/HeJ, CAST/EiJ, CBA/J, DBA/J, DBA/2J, LP/J, NOD/ShiLtJ, NZO/HILtJ, PWK/PhJ, WSB/EiJ, MSM/Ms, JF1/Ms |
| Foxr1 | rs215230760 | + | 129S1/SvlmJ, CAST/EiJ, LP/J, PWK/PhJ, MSM/Ms, JF1/Ms |
| Cilp | rs262051220 | + | 129S1/SvlmJ, A/J, AKR/J, BALB/cJ, C3H/HeJ, C57BL/6NJ, CAST/EiJ, CBA/J, DBA/2J, FVB/NJ, LP/J, NOD/ShiLtJ, NZO/HILtJ, PWK/PhJ, SPRET/EiJ, WSB/EiJ, MSM/Ms, JF1/Ms |
| Slc22a21 | rs231568920 | − | NZO/HILtJ, PWK/PhJ, MSM/Ms, JF1/Ms |
| Clec10a[1] | | + | |
| Serpina3i | rs242560633 | − | 129S1/SvlmJ, AKR/J, BALB/cJ, CBA/J, DBA/2J, FVB/NJ, LP/J, NOD/ShiLtJ, WSB/EiJ |
| Zkscan4 | rs249591363 | + | A/J, AKR/J, BALB/cJ, C3H/HeJ, CAST/EiJ, CBA/J, DBA/2J, FVB/NJ, LP/J, NOD/ShiLtJ, WSB/EiJ |
| Zfp957 | rs249051530 | − | 129S1/SvlmJ, A/J, AKR/J, BALB/cJ, C3H/HeJ, CBA/J, FVB/NJ, LP/J, NZO/HILtJ, PWK/PhJ |
| Timm8a2 | rs237108606 | − | 129S1/SvlmJ |
| Pdzd2[1] | | + | |
| Cyp2d11 | | + | 129S1/SvlmJ3, A/J3, AKR/J3, BALB/cJ3, C3H/HeJ3, CBA/J3, DBA/2J3, LP/J3, NOD/ShiLtJ3, NZO/HILtJ3 |
| Kcnk7 | | + | A/J, AKR/J, BALB/cJ, C3H/HeJ, NOD/ShiLtJ, PWK/PhJ, SPRET/EiJ, MSM/MS, JF1/Ms |

Mutations of 7 genes specifically present in NC/Nga mice are indicated in bold.
"Last Exon" means that a mutation is located in the last exon of the corresponding transcript.
Rs262301704 corresponds to c, 1157_1158insCCCA and a mouse with rs262301704 is indicated by *.

Figure 5:
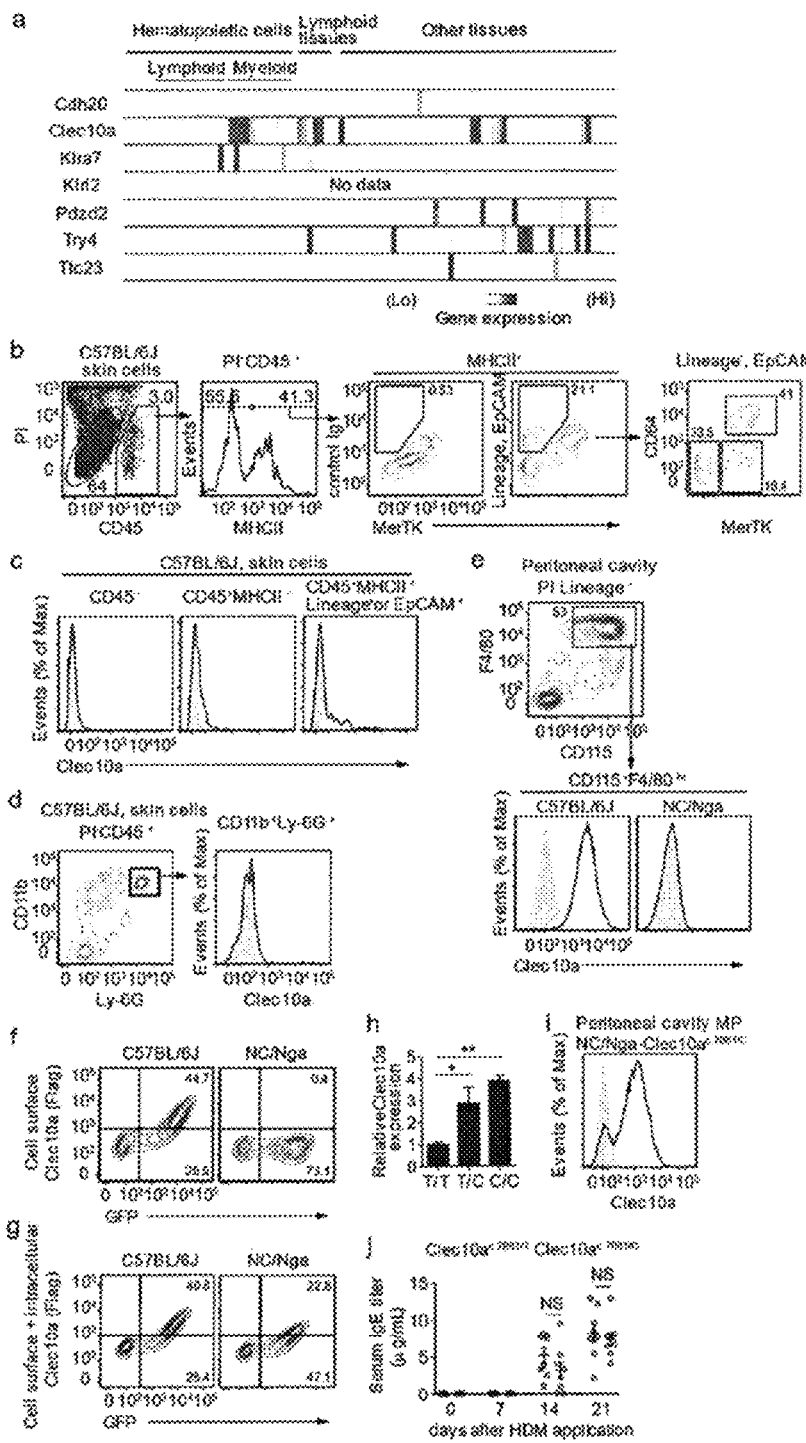
FIG. 5 shows results of characterization of Clec10a in C57BL/6J mice and NC/C57BL mice. Panel a shows results of gene expression in hematopoietic cells and tissue in C57BL/6J mice based on BioGPS analysis. Although these genes show a nonsense mutation or a frameshift mutation only in NC/Nga mice, such a mutation was not observed in other 19 mouse strains. Panels b to e and i show results of flow cytometry analysis of cells isolated from the dorsal skin (panels b, c, and d) or abdominal (panels e and i) of C57BL/6J mice, NC/Nga mice, and NC/Nga-Clec10a$^{c.706T/C}$ mice. The cells were stained with propidium iodide (Pi), antibodies against designated markers, and anti- Clec10a antibodies or control antibodies. The Lineage indicates CD3, CD19, NK1.1, and Ly-6G. A shaded histogram shows staining with an isotype control antibody. Panels f and g show results of surface analysis for transformants of RAW264.7 expressing Flag-tagged $Clec10a^{c.706C}$-IRES-GFP or Flag-tagged $Clec10a^{c.706T}$-IRES-GFP (panel f) and intracellular expression of the Flag tag by flow cytometry (panel g). Panel h shows expression of Clec10a mRNA in the skin of NC/Nga $Clec10a^{c.706T/T}$ (T/T), $Clec10a^{c.706T/C}$ (T/C), and $Clec10a^{c.706C/C}$ (C/C) mice. Panel j shows results of comparison between $Clec10a^{c.706T/T}$ (T/T) and $Clec10a^{c.706T/C}$ (T/C) in terms of serum IgE values at designated time points. * represents p<0.05,  represents p<0.01, and * represents p<0.001 (one-sided ANOVA test). Data indicates mean±SEM.

Mutations present in 17 inbred mouse lines and two Japanese pet mice were excluded, and seven mutations in seven genes were noted. (See the bold in Table 5). From the perspective of expression in hematopoietic cells, Clec10a was selected from the seven genes based on BioGPS database information (see panel a in FIG. 5). Clec10a of the NC/Nga mice was a nonsense mutation (i.e. Q236X) where the 706th C in the base sequence of NM_010769 was T (that is, Q 236X).

Example 2: Clec10a Expression Analysis and Functional Analysis

Clec10a is a member of the type II C-type lectin receptor family and detects galactose moieties at terminals of foreign and endogenous antigens. c.706C>T of Clec10a in the NC/Nga mice is present in the coding region of the C-type lectin-like domain (FIG. 1, panels a and b). The flow cytometric analysis revealed that Clec10a was expressed on the cell surface of macrophages (MP) (CD64$^+$MerTK$^+$), known dendritic cells (cDC) (CD64$^-$MerTK$^-$), and mononuclear cell-derived DCs (CD64$^-$MerTK$^{lo}$), as well as macrophages in the peritoneal cavity of C 57BL/6J (not expressed in the peritoneal cavity of NC/Nga mice), in skin CD45$^+$MHCII$^+$Lineage$^-$EpCAM$^-$cells (see panel c in FIG. 1 and panels b and e in FIG. 5). No expression of Clec10a was observed on non-hematopoietic cells (CD45$^-$), CD45$^+$ MHCII– cells, CD45$^+$MHCII$^+$(Lin, EpCAM)$^+$ cells, and neutrophils (CD45$^+$CD11b$^+$Ly-6G$^+$) of the skin of the C57BL/6J mice (see panels c and d in FIG. 5). Similar results were obtained by the immunohistochemistry staining, and expression of Clec10a was observed in skin cells of the C57BL/63 mice, but no expression was observed in the NC/Nga mice (panel d in FIG. 1).

The characteristics of Clec10a expression in the NC/Nga mice were further analyzed. Specifically, cDNA from Clec10a (from C57BL/6J and NC/Nga mice) with a Flag tag at the 3'end and a sequence encoding IRES-GFP was transfected into RAW264.7 macrophages. The Flag tag was expressed on the cell surface of the macrophages expressing Clec10a derived from the C57BL/6J mice, but not on the cell surface of macrophages expressing Clec10a from the NC/Nga mice. (See panel f in FIG. 5). However, in the macrophages expressing Clec10a from the NC/Nga mice, expression of Flag in the cells was observed (see panel g in FIG. 5). These results suggest that mutations in Clec10a negatively affected Clec10a transport to the cell surface.

This Clec10a mutation was then checked whether it is involved in dermatitis due to house dust mites (HDMs). Thus, instead of a native sequence (Clec10a$^{c.706T}$), a mutant mouse with Clec10a$^{c.706C}$ (hereafter, sometimes referred to as "NC/Nga mouse Clec10a$^{c.706T>C}$") was made according to a routine method using a CRISPR/Cas9 system (see panel a in FIG. 1). In the skin of the mutant mice with Clec10a$^{c.706C}$, Clec10a mRNA expression was significantly increased as compared with the mice with Clec10a$^{c.706T}$ (see panel h in FIG. 5). In mutant mice heterozygous for Clec10a$^{c.706T}$ and Clec10a$^{c.706C}$ (Clec10a$^{c.706T/C}$), Clec10a expression on the surface of macrophages in the skin and abdominal cavity was restored (see panels c and d in FIG. 1, and panel i in FIG. 5). In addition, symptoms of HDM-induced dermatitis, such as erythema, dryness, and increased skin thickness, were alleviated in the mutant mice (Clec10a$^{c.706T/C}$) (panels e to h in FIG. 1). Furthermore, neutrophil infiltration into the skin after six days of the HDM treatment was reduced in the mutant mice (Clec10a$^{c.706T/C}$) as compared with NC/Nga mice with wild type Clec10a (Clec10a$^{c.706T/T}$) (panel i in FIG. 1). In contrast, the IgE serum levels of both the mice were comparable. These results suggest that Clec10a mutants (Clec10a$^{c.706TC}$) cause HDM-induced dermatitis and not increase Th2 response in the NC/Nga mice.

To investigate the involvement of cell surface expression of Clec10a in HDM-induced dermatitis, Clec10a-deficient mice (Clec10a$^{-/-}$ mice) were made using C57BL/6J mice as a background. HDM was applied topically to the dorsal skin of the wild type C57BL/6J mice and the Clec10a-deficient mice (Clec10a$^{-/-}$). As observed in the skin of the NC/Nga mice, the Clec10a–/– mice showed exacerbations of dermatitis, such as erythema, dryness and skin enhancement on Days 5 to 6 after the HDM treatment, as compared with the wild type mice (see panels a to d in FIG. 2). In addition, on Days 1 to 3 after the HDM treatment, the Clec10a–/– mice showed an increase in neutrophil infiltration in the skin (see panel e in FIG. 2). In contrast, the wild type mice and the Clec10a–/– mice were equivalent in number of cells in other bone marrow and lymphocytic systems (see panel a in FIG. 6).

Figure 6:
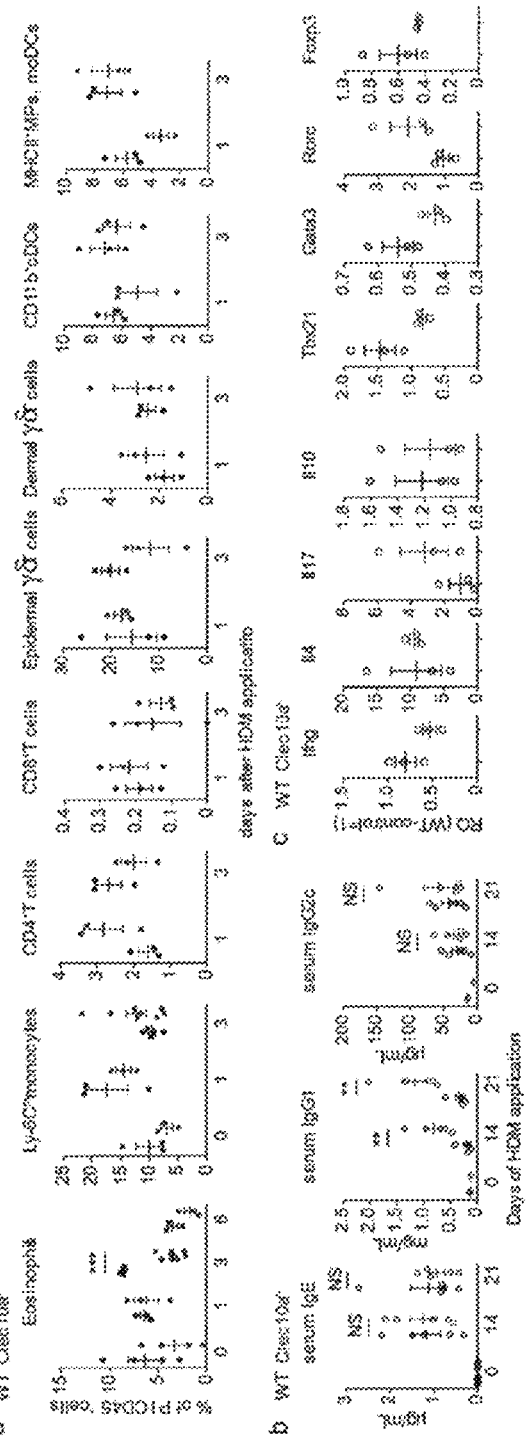
FIG. 6 shows a phenotype of HDM-induced dermatitis in Clec10a-deficient mice. A house dust mite (HDM) ointment was applied twice weekly to the dorsal skin of wild type C57BL/6J mice and Clec10a−/− mice. Panel a shows results of flow cytometry analysis of each cell population after staining the skin cells collected at designated time points with an antibody against a Pi, an anti CD45 antibody, or a marker molecule. Markers for each cell were as follows: eosinophils (CD11b⁺Siglec-F⁺) and Ly-6C$^{hi}$ monocytes (CD11b⁺Ly-6G-Siglec-F-Ly-6C$^{hi}$), CD3+CD4+ T cells (CD3⁺CD4⁺), CD8+ T cells (CD3+CD8+), epithelial γδ T cells (CD3$^{hi}$TCRγδ$^{hi}$), dermal γδ T cells (CD3$^{mid}$TCRγδ$^{mid}$), CD11b⁺ known dendritic cells (cDC) (CD11b⁺MHCII⁺CD11c⁺CD64⁻), MHCII⁺ macrophages (MPs), monocyto-derived DC (CD11b⁺MHCII⁺CD11c⁻CD64⁺). Panel b is an ELISA of serum Ig value at designated time points (n=5). Panel c shows results of quantitative RT-PCR of mRNA expression levels of designated molecules in wild type and Clec10a−/−type CD4+ T cells (CD3⁺CD4⁺) sorted from axillary lymph nodes and inguinal lymph nodes on Day 6.  represents p<0.01 and * represents p<0.001 (independent two-sided Student's t-test). Data indicates mean±SEM.

At two weeks after the HDM treatment, the serum IgG1 level was higher in the Clec10a–/– mice than in the wild type, and the IgE and IgG2c values were comparable between the wild type and the Clec10a–/– mice (see panel b in FIG. 6). In addition, expression of Il4 and Gata3 CD4$^+$ T cells in the HDM-treated skin draining lymph node was comparable between the wild type and the Clec10a–/– mice (see panel c in FIG. 6). Therefore, it is believed that Clec10a suppresses dermatitis by reducing neutrophil infiltration rather than reducing the Th2 response.

Figure 7:
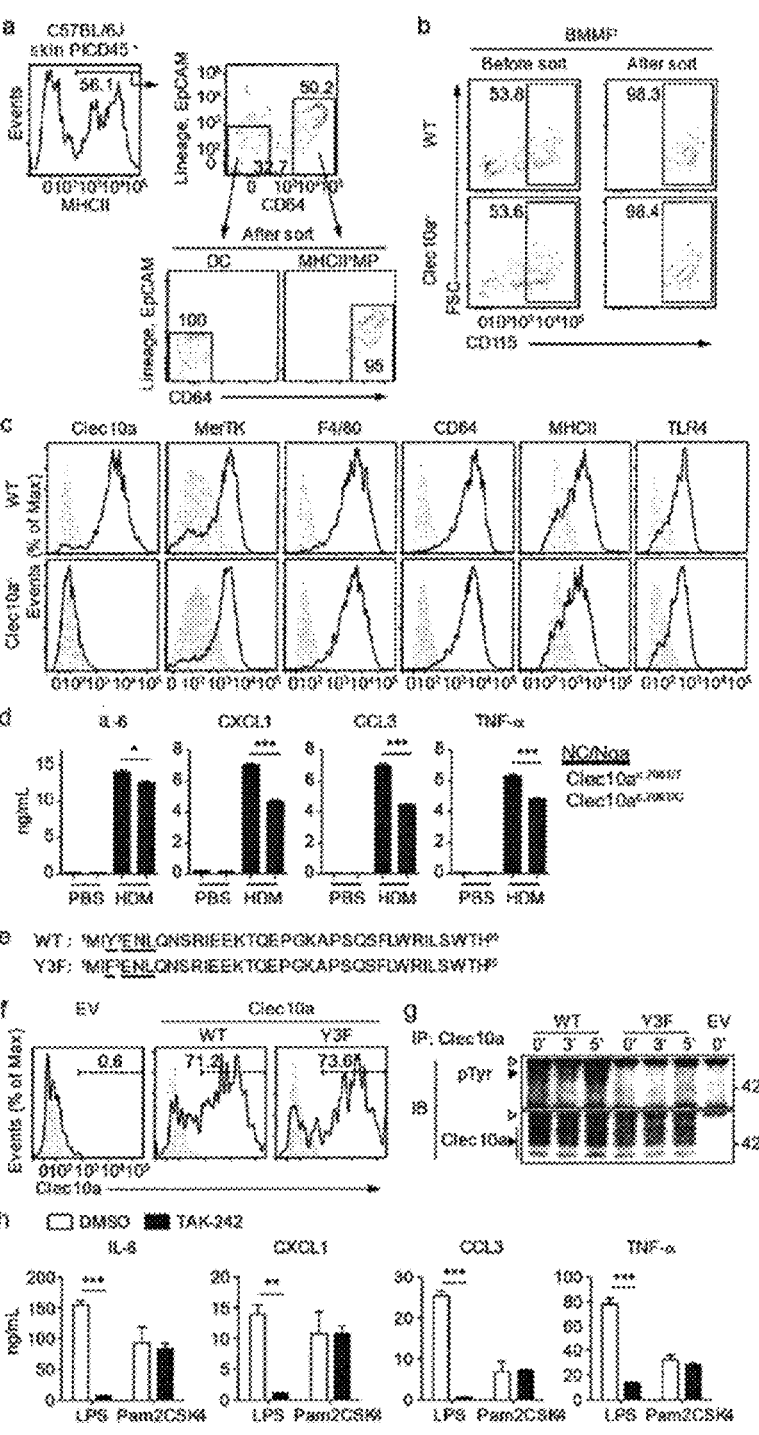
FIG. 7 shows results of characterization of wild type MP and Clec10a−/−type MP. Panel a shows the gating strategy for sorting of MP (PI-CD45⁺MHCII⁺Lineage (CD3, CD19, NK1.1, and Ly-6G) ⁻EpCAM⁻CD64⁺) and DC (PI⁻CD45⁺MHCII⁺Lineage⁻EpCAM⁻CD64⁻) obtained from mouse skin 3 hours after topical application of HDM. Panel b shows gate strategy for sorting CD115⁺ BMMP from the wild type mice and the Clec10a−/−type mice. Panel c shows results of staining of BMMP derived from the wild type mice and the Clec10a−/−type mice with CD115, Clec10a, designated MP markers and antibodies against TLR4. CD115⁺ cells were gated and the expression of each molecule was analyzed by flow cytometry. A shaded histogram shows staining with an isotype control antibody. Panel d shows results of cytometric bead array (CBA) analysis of culture supernatants of BMMPs derived from $Clec10a^{c.706T/T}$ (T/T) mice and $Clec10a^{c.706T/C}$ (T/C) mice after HDM stimulation (n=3). Panel e shows amino acid sequences of intracellular regions of Clec10a of wild type and Y3F mutant. Deduced hemITAM sequences are underlined. Panels f and g show expression of Clec10a on cell surface of BMMP transfected with cDNA encoding Clec10a of wild-type and Y3F mutant or an empty vector. A shaded histogram shows staining with an isotype control antibody (panel f). Transfected cells were stimulated with HDM, lysed, immunoprecipitated (IP) with anti-Clec10a antibodies, and immunoblotted with anti-phosphorylated tyrosine (pTyr) antibodies and anti-Clec10a antibodies (panel g). An arrowhead indicates a molecule of interest (black) and an antibody (IP-Ab) used in IP (white). Panel h shows results of CBA analysis of cell supernatants from CD115+ BMMP treated with 0.5 μM TAK-242 or DMSO after stimulation with 1 ng/ml LPS or 200 pg/ml Pam2CSK4 for 6 hours.  represents p<0.01 and * represents p<0.001 (independent two-sided Student's t-test). Data indicates mean±SEM (n=3).

Since Clec10a was expressed in MHCII$^+$ macrophages (MPs) and dendritic cells (DCs) of the skin, these cells were sorted from skin cell samples of topically-HDM-treated wild type and Clec10a–/– mice (see panel a in FIG. 7). Gene expression levels of Il6, Cxcl1, and Cxcl2 were higher in the Clec10a–/– MP than in the wild type MP, but these gene expression levels were comparable between the wild type DC and the Clec10a–/– DC (see panel f in FIG. 2). These results suggest that Clec10a in MP is involved in suppression of HDM-induced dermatitis more than in DC. Bone marrow macrophages (BMMPs) were prepared from the wild type mice and the Clec10a–/–C57BL/6J mice, respectively, and characterized (see panel b in FIG. 7). The expression levels of MP marker and TLR4 in CD115$^+$ BMMP were comparable between the wild type mice and the Clec10a–/–mice. After in vitro HDM stimulation, the Clec10a–/– BMMP secreted a larger amount of neutrophil chemotactic substances, such as IL-6, CXCL1, CCL3 and TNF-α, than the wild type BMMP (see panel g in FIG. 2). Similarly, BMMP of the Clec10a$^{c.706T/T}$ NC/Nga mice showed a larger amount of cytokine production than BMMP in the Clec10a$^{c.706T/C}$ (see panel d in FIG. 7). These results demonstrated that the expression of Clec10a on the cell surface inhibits the production of inflammatory cytokines from the skin MP following stimulation with HDM.

Figure 2:
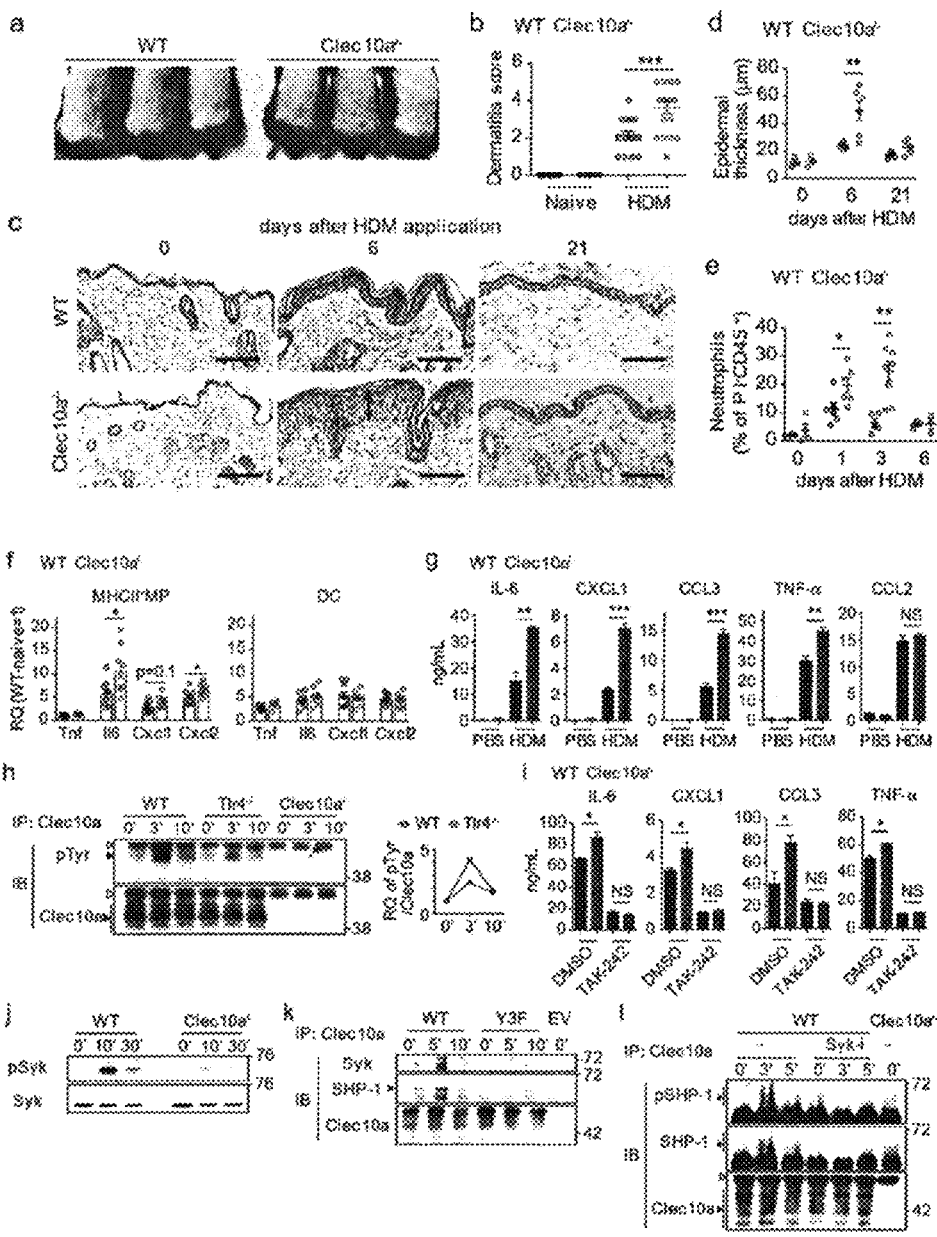
FIG. 2 shows that Clec10a inhibits HDM-induced immune responses. Panels a-f show results of applying an HDM ointment to the dorsal skin of C57BL/6J wild type mice and Clec10a$^{-/-}$ mice twice weekly. Panels a and b show tissue and epithelial thickness, respectively, at specific time points (n=3, 6, 5). Panels c and d show comparison between the wild type mice and the Clec10a$^{-/-}$ mice. Panel e shows flow cytometry for identifying neutrophils (CD11b$^+$ Ly-6g$^+$) in the skin CD45+ cells of the wild type mice and the Clec10a$^{-/-}$ mice at specific time points. Panel f shows results of quantitative RT-PCR of mRNA obtained from MHCII+ MPs and DCs of the WT and the Clec10a$^{-/-}$ at 3 hours after topical application of HDM. Panel g shows results of cytometric bead array (CBA) analysis of culture supernatants from HDM-stimulated wild-type or Clec10a$^{-/-}$ CD115+ enriched BMMPs (n=3). Panel h shows results of stimulating wild-type, Tlr 4–/–, and Clec10a–/– BMMPs with HDM for a designated time, followed by immunoprecipitation (IP) of lysates thereof with a Clec10a antibody. Immunoblot analysis (IB) was performed using antibodies against phosphorylated tyrosine (pTyr) or Clec10a. Panel i shows results of cytometric bead array (CBA) analysis of culture supernatants from wild-type or Clec10a–/– CD115+ enriched BMMPs pre-treated with 0.5 μM TAK-242 and stimulated with HDM for 6 h (n=3). Panel j shows results of stimulating wild-type or Clec10a–/– CD115+ enriched BMMPs with HDM for a designated time, followed by immunoblot (TB) with phosphorylated Syk (pSyk; Y$^{519/520}$) or a monoclonal antibody against Syk (mAb). Panel k shows results of stimulating, with HDM, BMW's transfected with wild-type or Y3F Clec10a or with an empty vector (EV), and immunoprecipitating cell lysates with mAb against Clec10a, followed by immunoblot with an antibody against Syk, SHP-1 or Clec10a. Panel l shows results of pretreating wild-type and Clec10a–/– BMMPs with Syk inhibitor IV, stimulating the BMMPs with HDM for a designated time, and immunoprecipitating (IP) cell lysates with an antibody against Clec10a, followed by immunoblot with an antibody against pSHP-1, SHP-1 or Clec10a. An arrowhead indicates a molecule of interest (black) or a heavy chain of IP-Ab (white). * represents $p<0.05$,  represents $p<0.01$, and * represents $p<0.001$ (independent two-sided Student's t-test). Data indicates mean±SEM.

HDM stimulation caused activation of spleen tyrosine kinase (Syk) in the wild type BMMP, but no activation of Syk was observed in the Clec10a–/– BMMP (see panel j in FIG. 2). In addition, HDM stimulation caused the recruitment of Syk and protein tyrosine phosphatase SHP-1 to Clec10a, and the recruitment relied upon Clec10a tyrosine residues (see panel k in FIG. 2). BMMP treatment with Syk inhibitors suppressed the recruitment of HDM-induced SHP-1 to Clec10a (panel 1 in FIG. 2), suggesting that the event relies on Syk activation. The results were consistent with control signaling via inhibitory ITAM.

Example 3: Analysis of Clec10a Ligand

Figure 3:
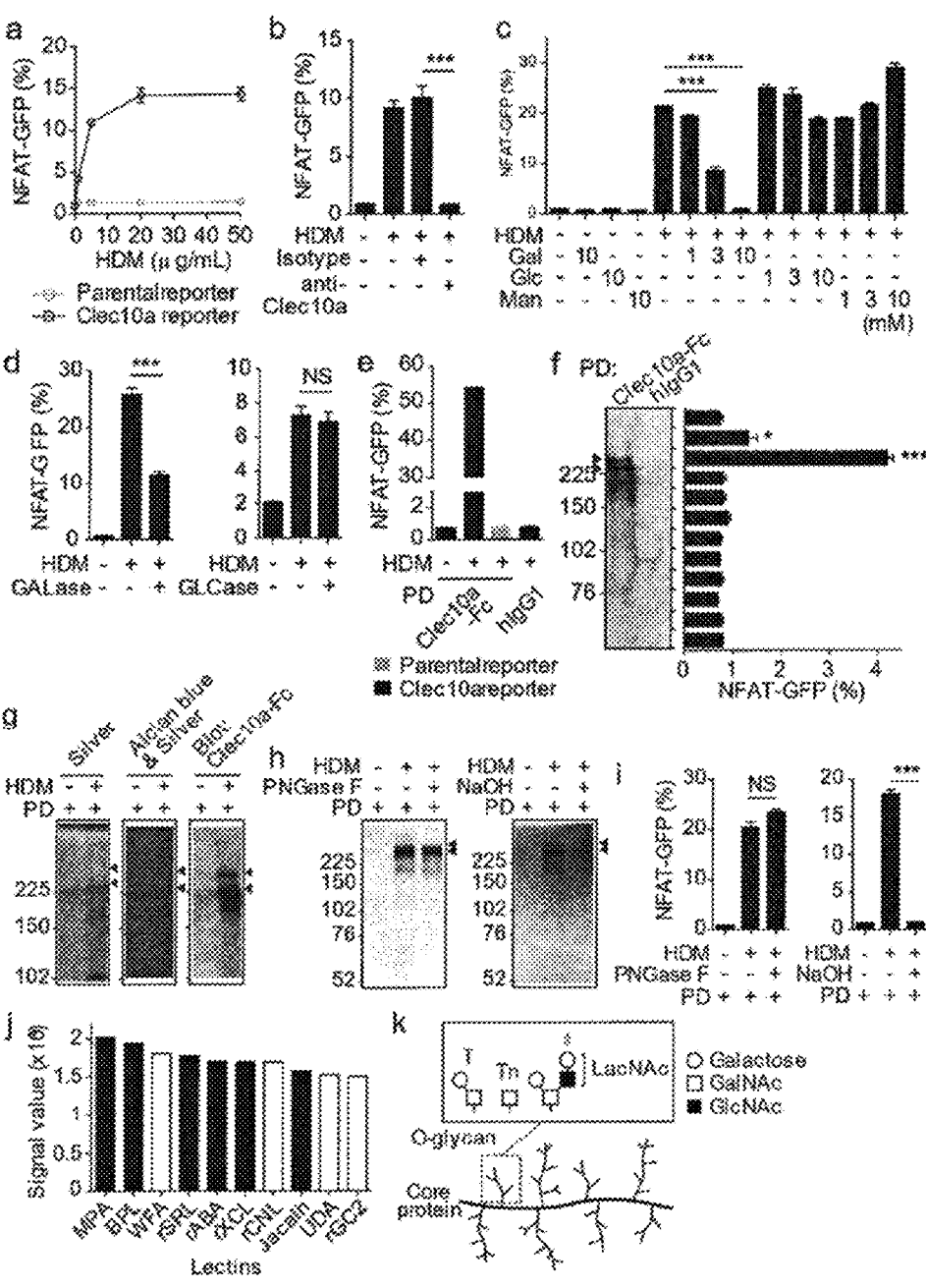
FIG. 3 shows that Clec10a recognizes a mucin-like protein of HDM. Panels a to d show expression of GFP: after stimulation with HDM-coated plates in the presence or absence of rat IgG2a or anti-Clec10a mAb (panels a and b), or galactose (Gal), glucose (Glc) or mannose (Man) (panel c); or after stimulation with HDM-coated plates treated with galactosidase (GALase) or glucosidase (GLCase) or untreated (panel d), in mouse Clec10a-CD3ζ reporter cells or parent reporter cells. Panels e to i show expression of GFP in mouse Clec10a-CD3ζ reporter cells or control reporter cells after stimulation with Clec10a ligand (Clec10a-L) in HDM pulled down (PD) with Clec10a-Fc or control human antibody (panel e), each fraction based on the size of Clec10a-L (panel f), or Clec10a-L before or after treatment with PNGase F or NaOH (panel i). Statistical analysis was performed using PBS-stimulated samples used as controls (panel f). Clec10a-L was immunoblotted using Clec10a-Fc before treatment with PNGase F or NaOH (panels f to h) or after treatment (panel h), or silver-stained with or without alcian blue (panel g). Panel j shows lectin microarray analysis of Clec10a-L. The black bars indicate a lectin binding to Galβ(1-3)GalNAc (T antigen). GalNAc means N-acetylgalactosamine and GlcNAc means N-acetylglu-cosamine. Panel k shows a schematic representation of Clec10a-L in HDM. T means a T antigen (Galβ(1-3)Gal-NAc), Tn means a Tn antigen (αGalNAc) and LacNAc means N-acetyl-D-lactosamine (Galβ(1-4)GlcNAc). * represents $p>0.05$,  represents $p>0.01$, and * represents $p>0.001$ (one-sided ANOVA test (panels c and f) or independent two-sided Student's t-test (panels b, d, and i)). Data indicates mean±SEM (n=3).

To test whether Clec10a recognized glycosylated proteins contained in HDM, NFAT-GFP reporter cells (Clec10a reporter cells) were made which expressed chimeric fusion proteins inch ling an extracellular and transmembrane portions of Clec10a fused to a cytoplasmic portion of CD3. Mouse Clec10a reporter cells expressed GFP in response to Lewis X (Clec10a oligosaccharide ligand) but did not respond to Lewis Y (see panels a and b in FIG. 8). The mouse Clec10a reporter cells also expressed GFP in response to the HDM-coated plate dose-dependently (panel a in FIG. 3). In addition, pretreatment of the reporter cells with anti-Clec10a monoclonal antibodies (mAb) or galactose inhibited GFP expression, but glucose or mannose pretreatment did not suppress GFP expression (panels b and c in FIG. 3). Furthermore, treatment of HDM with galactosidase reduced their ability to cause GFP expression in the reporter cells, but no such reduction was observed when glucosidase was used (panel d in FIG. 3). These results indicate that Clec10a directly binds to the galactosylated moiety of HDM.

Figure 8:
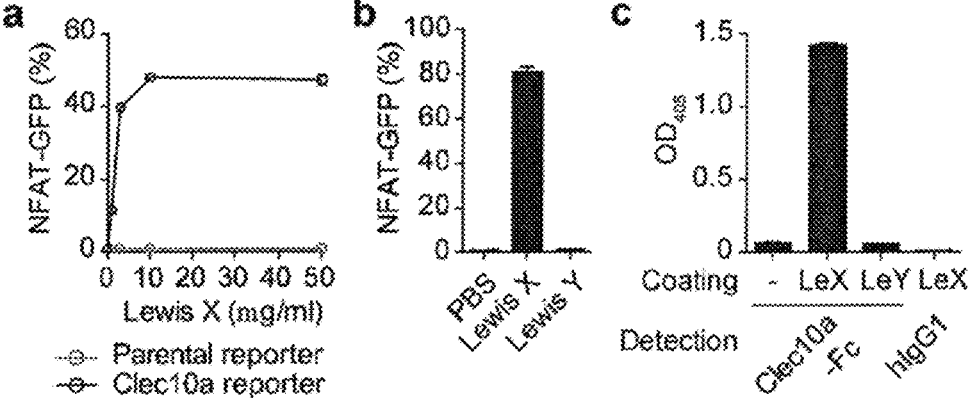
FIG. 8 shows establishment of a Clec10a-CD3ζ reporter cell and a Clec10a-FC chimeric protein. Panels a and b show results of flow cytometry analysis of GFP expression of Clec10a-CD3ζ reporter cells after stimulation with plates coated with Lewis X and Lewis X (10 μg/mL) or Lewis Y (10 μg/mL) at the specified doses (panel a). Panel c shows results of ELISA analysis of Clec10a-Fc bound to the plates coated with Lewis X (LeX) or Lewis Y (LeY). Data indicates mean±SEM (n=3).

For analysis of the Clec10a ligand (Clec10a-L) in HDM, chimeric fusion proteins including an extracellular portion (Clec10a-Fe) of mouse Clec10a fused to the Fc portion of human IgG1 were made, but the fusion proteins were not bound to Lewis Y but were bound to Lewis X (panel c in FIG. 8). Pull-down assays from HDM using Clec10a-Fc isolated Clec10a-L having a molecular weight of about 225 kDa, but Clec10a-L was able to induce expression of GFP in the mouse Clec10a reporter cells (see panels e and f in FIG. 3). Clec10a-L was stained with alcian blue and silver but not stained with silver alone (see panel g in FIG. 3), indicating that Clec10a-L is a highly sugar-modified protein. Treatment with NaOH to degrade the O-linked glycans inhibited the binding of Clec10a-Fc to the epitope (see panel h in FIG. 3) and inhibited the induction of GFP expression in the mouse Clec10a reporter cells (see panel i in FIG. 3). In contrast, PNGase F, which degrades N-linked glycans, did not show any effect on Clec10a-L (see panels h and i in FIG. 3). These results suggest that Clec10a recognizes the O-linked glycans of Clec10a-L. Analysis by the lectin microarray also showed that Clec10a-L contains a T antigen (Galβ(1-3)GalNAc) and a Tn antigen (αGalNAc) and has an LacNAc epitope (Galβ (1-4)GlcNAc) binding to mucin-type O glycans (panel j in FIG. 3, and Table 6).

TABLE 6

| | | Lectin microarray analysis of Clec10a ligand in HDM | | | |
| | | | Signal value | | |
| Rank | Lectin | Rough specificity | Target[1] | Control1[2] | Control2[3] |
|---|---|---|---|---|---|
| 1 | MPA | Galβ1-3GalNAc (T), αGalNAc (Tn) | 20283 | 0 | 0 |
| 2 | BPL | Galβ1-3GalNAc (T), terminal GalNAc | 19440 | 0 | 0 |
| 3 | WFA | Terminal GalNAc, LacDiNAc | 18081 | 0 | 0 |
| 4 | rSRL | Galβ1-3GalNAc (T), GlcNAcβ1-3GalNAc, agalacto N-glycan | 17794 | 0 | 0 |
| 5 | rABA | Galβ1-3GalNAc (T), GlcNAc | 17018 | 0 | 0 |
| 6 | rxCL | Galβ1-3GalNAc (T), GlcNAcβ1-3GalNAc, aGalacto N-glycan | 16918 | 0 | 0 |
| 7 | rCNL | Terminal GalNAc (A, Tn, LacDiNAc) | 16900 | 0 | 0 |
| 8 | Jacalin | Galβ1-3GalNAc (T), αGalNAc (Tn) | 15697 | 0 | 0 |
| 9 | UDA | (GlcNAc)n | 15228 | 0 | 0 |
| 10 | rGC2 | α1-2Fuc (H), αGalNAc (A), αGal (B) | 15049 | 0 | 0 |
| 11 | RCA120 | βGal | 14050 | 0 | 0 |
| 12 | rPSL1a | α2-6Sia | 13311 | 0 | 0 |
| 13 | SBA | α, βGalNAc (A, Tn, LacDiNAc) | 12337 | 0 | 0 |
| 14 | ABA | Galβ-3GalNAc (T), GlcNAc | 11636 | 0 | 0 |
| 15 | rCGL2 | GalNAcα1-3Gal (A), PolyLacNAc | 10999 | 1370 | 0 |
| 16 | PNA | Galβ1-3GalNAc (T) | 10699 | 0 | 0 |
| 17 | TJAII | β1-2Fuc | 10518 | 0 | 0 |
| 18 | VVA! | GalNAcβ1-3(4)Gal | 10377 | 0 | 0 |
| 19 | HEA | Galβ1-3GalNAc (T) | 9936 | 0 | 0 |
| 20 | rGal9N | GalNAcα1-4Gal (A), PolyLacNAc | 9093 | 0 | 0 |
| 21 | rLSLN | LacNAc, polylactosamine | 8962 | 0 | 0 |
| 22 | MCA | α1-2Fuc | 8239 | 0 | 0 |
| 23 | ACA | Galβ1-3GalNAc (T) | 8057 | 0 | 0 |
| 24 | rGal9C | PolyLacNAc, Branched LacNAc | 7990 | 0 | 0 |
| 25 | rAAL | α1-2Fuc (H), α1-3Fuc (Lex), α1-3Fuc (Lea) | 7764 | 0 | 0 |
| 26 | AAL | α1-2Fuc (H), α1-3Fuc (Lex), α1-4Fuc (Lea) | 7508 | 0 | 0 |
| 27 | VVA | a, βGalNAc (A, Tn, LacDiNAc) | 6765 | 0 | 0 |
| 28 | rACG | α2-3Sia | 6442 | 0 | 0 |
| 29 | rBC2LCN | Fucα1-2Galβ1-3GlcNAc (GalNAc) | 5909 | 0 | 0 |
| 30 | HPA | αGalNAc (A, Tn) | 5471 | 0 | 0 |
| 31 | GNA | Manα1-3Man, Manα1-6Man | 4458 | 0 | 0 |
| 32 | NPA | Manα1-3Man | 3993 | 0 | 0 |
| 33 | ECA | βGal | 3871 | 0 | 0 |
| 34 | DBAI | High-man | 3793 | 0 | 0 |
| 35 | rRC2LA | αMan, High-man | 3766 | 0 | 0 |
| 36 | PVL | Sia, GlcNAc | 3729 | 0 | 0 |
| 37 | rRSIIL | α1-2Fuc (H), α1-3Fuc (Lex), α1-3Fuc (Lea) | 3678 | 0 | 0 |
| 38 | rMOA | αGal (B) | 3656 | 0 | 0 |
| 39 | rGRFT | Man | 3502 | 0 | 0 |

TABLE 6-continued

| | | | Signal value | | |
|---|---|---|---|---|---|
| Rank | Lectin | Rough specificity | Target[1] | Control1[2] | Control2[3] |
| 40 | rAOL | α1-2Fuc (H), α1-3Fuc (Lex), α1-3Fuc (Lea) | 3194 | 0 | 0 |
| 41 | CCA | Galactosylated N-glycans up to triantenna | 3093 | 0 | 0 |
| 42 | LEL | Polylactosamine, (GlcNAc)n | 3054 | 0 | 0 |
| 43 | STL | Polylactosamine, (GlcNAc)n | 2611 | 0 | 0 |
| 44 | rPPL | a, βGalNAc (A, Tn, LacDiNAc) | 2579 | 0 | 0 |
| 45 | rPALa | Man5, biantenna | 2493 | 0 | 0 |
| 46 | GSLIA4 | αGalNAc (A, Tn) | 2181 | 0 | 0 |
| 47 | HHL | Manα1-3Man, Manα1-7Man | 1731 | 0 | 0 |
| 48 | rDiscoidinII | LacNAc, Galβ1-3GalNAc (T), GalNAc (Tn) | 1306 | 0 | 0 |
| 49 | DSA | GlcNAcβ1-6Man (Tetraantenna) | 1095 | 0 | 0 |
| 50 | SSA | α2-6Sia | 1013 | 0 | 0 |
| 51 | TxLcl | Galactosylated N-glycans up to triantenna | 973 | 0 | 0 |
| 52 | rDiscoidinI | Gal | 737 | 0 | 0 |
| 53 | rCalsepa | Biantenna with bisecting GlcNAc | 651 | 0 | 0 |
| 54 | rGal3C | LacNAc, polylactosamine | 630 | 0 | 0 |
| 55 | WGA | (GlcNAc)n, polySia | 624 | 0 | 0 |
| 56 | PSA | α1-6Fuc up to biantenna | 481 | 0 | 0 |
| 57 | AOL | α1-2Fuc (H), α1-3Fuc (Lex), α1-3Fuc (Lea) | 309 | 0 | 0 |
| 58 | LCA | α1-6Fuc up to biantenna | 228 | 0 | 0 |
| 59 | rPAIIL | αMan, α1-2Fuc (H), α1-3Fuc (Lex), α1-4Fuc (Lea) | 131 | 0 | 0 |
| 60 | TJAI | α2-6Sia | 113 | 0 | 0 |
| 61 | rBanana | Manα1-2Manα1-3(6)Man | 10 | 0 | 0 |
| 62 | ASA | Galβ1-4GlcNAcβ1-2Man | 2 | 0 | 0 |
| 62 | rCGL3 | LacDiNAc | 2 | 0 | 0 |
| 64 | LFA | Sia | 0 | 0 | 0 |
| 64 | MAL | α2-3Sia | 0 | 0 | 0 |
| 64 | MAH | α2-3Sia | 0 | 0 | 0 |
| 64 | ACG | α2-3Sia | 0 | 0 | 0 |
| 64 | rGal8N | α2-3Sia | 0 | 0 | 0 |
| 64 | SNA | α2-6Sia | 0 | 0 | 0 |
| 64 | ADA | α2-6Sia, Forssman, A, B | 0 | 0 | 0 |
| 64 | PHAL | GlcNAcβ1-6Man (Tetraantenna) | 0 | 0 | 0 |
| 64 | rGal7 | Type1 LacNAc, chondroitin polymer | 0 | 0 | 0 |
| 64 | rC14 | Branched LacNAc | 0 | 0 | 0 |
| 64 | PHAE | bisecting GlcNAc | 0 | 0 | 0 |
| 64 | GSLII | GlcNAcβ1-4Man | 0 | 0 | 0 |
| 64 | PWM | (GlcNAc)n | 0 | 0 | 0 |
| 64 | rF17AG | GlcNAc | 0 | 0 | 0 |
| 64 | ConA | M3, Manα1-2Manα1-3(Manα1-6)Man, GlcNAcβ1-2Manα1-3(Manα1-6)Man | 0 | 0 | 0 |
| 64 | Heltuba | Manα1-3Man | 0 | 0 | 0 |
| 64 | rHeltuba | Manα1-3Man | 0 | 0 | 0 |
| 64 | VVAII | Man, agalacto | 0 | 0 | 0 |
| 64 | rOrysata | Manα1-3Man, Highman, biantenna | 0 | 0 | 0 |
| 64 | rRSL | αMan, α1-2Fuc (H), α1-3Fuc (Lex), α1-4Fuc (Lea) | 0 | 0 | 0 |
| 64 | rPTL | α1-6Fuc | 0 | 0 | 0 |
| 64 | LTL | Lex, Ley | 0 | 0 | 0 |
| 64 | UEAI | α1-2Fuc | 0 | 0 | 0 |
| 64 | FLAG-EW29Ch | Gal | 0 | 0 | 0 |
| 64 | PTLI | αGalNAc (A, Tn) | 0 | 0 | 0 |
| 64 | GSLIB4 | αGal (B) | 0 | 0 | 0 |
| 64 | EEL | αGal (B) | 0 | 0 | 0 |
| 64 | rPAIL | a, βGal, αGalNAc (Tn) | 0 | 0 | 0 |
| 64 | DBA | a, βGalNAc (A, Tn, LacDiNAc) | 0 | 0 | 0 |
| 64 | DBAIII | Maltose | 0 | 0 | 0 |
| 64 | rMalectin | Glcα1-2Glc | 0 | 0 | 0 |
| 64 | CSA | Rhamnose, Galα1-4Gal | 0 | 0 | 0 |
| 64 | FLAG-EW29Ch-E20K | 6-sulfo-Gal | 0 | 0 | 0 |

Lectin microarray analysis of Clec10a ligand in HDM

[1]Target: Pull-down assay sample from HDM using Clec10a-Fc
[2]Control 1: Pull-down assay sample from buffer using Clec10a-Fc
[3]Control 2: Pull-down assay sample from HDM using human IgG1

Clec10a was most strongly bound to the lectins of Maclura pomifera (MPA) recognizing high density of multivalent T and Tn antigens. On the other hand, analysis by glycan microarray revealed that Clec10a-Fc binds to T and Tn antigens (see Table 7) and suggested that Clec10a-L is a mucin-like protein (see panel k in FIG. 3).

TABLE 7

| | | | Signal value | | |
|---|---|---|---|---|---|
| Rank | Glycan | Structure | Clec10a-Fc | human IgG1 | Clec10a-Fc with EDTA |
| 1 | αGal | Galα1 | 11934 | 0 | 0 |
| 2 | Lea | Galβ1-3(Fucα1-4)GalNAcβ1 | 5532 | 0 | 0 |
| 3 | Lac | Galβ1-4Glcβ1 | 4850 | 0 | 0 |
| 4 | Core2 | Galβ1-3(GlcNAcβ1-6)GalNAcα1 | 4824 | 0 | 0 |
| 5 | Galα1-3LN | Galα1-3Galβ1-4GlcNAcβ1 | 4342 | 0 | 0 |
| 6 | Lex | Galβ1-4(Fucα1-3)GlcNAcβ1 | 2535 | 0 | 0 |
| 7 | T (Core1) | Galβ1-3GalNAcα1 | 2504 | 0 | 0 |
| 8 | Lec | Galβ1-3GlcNAcβ1 | 2414 | 0 | 0 |
| 9 | βGal | Galβ1 | 1867 | 0 | 0 |
| 10 | Galα1-4LN | Galα1-4Galβ1-4GlcNAcβ1 | 1679 | 0 | 0 |
| 11 | A-di | GalNAcα1-3Galβ1 | 1137 | 0 | 0 |
| 12 | Tn | GalNAcα1 | 682 | 0 | 0 |
| 13 | Galα1-3Lac | Galα1-3Galβ1-4Glcβ1 | 444 | 0 | 0 |
| 14 | Galα1-3Gal | Galα1-3Galβ1 | 144 | 0 | 0 |
| 15 | di-GalNAcβ | GalNAcβ1-3GalNAcβ1 | 65 | 0 | 0 |
| 16 | Melibiose | Galα1-6Glcβ1 | 45 | 0 | 0 |
| 17 | Sia3 | Neu5Acα2-8Neu5Acα2-8Neu5Acα2 | 19 | 0 | 3 |
| 18 | 3'SLN | Neu5Acα2-3Galβ1-4GlcNAcβ1 | 7 | 0 | 0 |
| 18 | LN | Galβ1-4GlcNAcβ1 | 7 | 0 | 0 |
| 20 | βGalNAc | GalNAcβ1 | 6 | 0 | 0 |
| 21 | 3'SL | Neu5Acα2-3Galβ1-4Glcβ1 | 5 | 0 | 0 |
| 22 | 3'SiaLec | Neu5Acα2-3Galβ1-3GlcNAcβ1 | 4 | 0 | 0 |
| 23 | βFuc | Fucα1 | 3 | 0 | 0 |
| 23 | [3S] βGal | (3OSO3)Galβ1 | 3 | 0 | 0 |
| 23 | Galα1-2Gal | Galα1-2Galβ1 | 3 | 0 | 0 |
| 26 | H type1 | Fucα1-2Galβ1-3GlcNAcβ1 | 1 | 0 | 0 |
| 26 | sLex | Neu5Acα2-3Galβ1-4(Fucα1-3)GlcNAcβ1 | 1 | 0 | 0 |
| 26 | 6'SL | Neu5Acα2-6Galβ1-4Glcβ1 | 1 | 0 | 0 |
| 26 | STn | Neu5Acα2-6GalNAcα1 | 1 | 0 | 0 |
| 30 | Fucα2Gal | Fucα1-2Galβ1 | 0 | 0 | 0 |
| 30 | Fucα3GlcNAc | Fucα1-3GlcNAcβ1 | 0 | 0 | 0 |
| 30 | Fucα4GlcNAc | Fucα1-4GlcNAcβ1 | 0 | 0 | 0 |
| 30 | H type2 | Fucα1-2Galβ1-4GlcNAcβ1 | 0 | 0 | 0 |
| 30 | H type3 | Fucα1-2Galβ1-3GalNAcβ1 | 0 | 0 | 0 |
| 30 | A | GalNAcα1-3(Fucα1-2)Galβ1-4GlcNAcβ1 | 0 | 0 | 0 |
| 30 | B | Galα1-3(Fucα1-2)Galβ1-4GlcNAcβ1 | 0 | 0 | 0 |
| 30 | [3S]Lea | (3OSO3)Galβ1-3(Fucα1-4)GlcNAcβ1 | 0 | 0 | 0 |
| 30 | Leb | Fucα1-2Galβ1-3(Fucα1-4)GlcNAcβ1 | 0 | 0 | 0 |
| 30 | Ley | Fucα1-2Galβ1-4(Fucα1-3)GlcNAcβ1 | 0 | 0 | 0 |
| 30 | Nêu5Ac | Neu5Acα2 | 0 | 0 | 0 |
| 30 | Nêu5Gc | Neu5Gcα2 | 0 | 0 | 0 |
| 30 | Siα2 | Neu5Acα2-8Neu5Acα2 | 0 | 0 | 0 |
| 30 | sLea | Neu5Acα2-3Galβ1-3(Fucα1-4)GlcNAcβ1 | 0 | 0 | 0 |
| 30 | [3'S]Lec | (3OSO3)Galβ1-3GlcNAcβ1 | 0 | 0 | 0 |
| 30 | [3'S]LN | (3OSO3)Galβ1-4GlcNAcβ1 | 0 | 0 | 0 |
| 30 | [6S]LN | Galβ1-4(6OSO3)GlcNAcβ1 | 0 | 0 | 0 |
| 30 | [6'S]LN | (6OSO3)Galβ1-4GlcNAcβ1 | 0 | 0 | 0 |
| 30 | LDN | GalNAcβ1-4GlcNAcβ1 | 0 | 0 | 0 |
| 30 | Gα2 | GalNAcβ1-4Galβ1-4Glcβ1 | 0 | 0 | 0 |
| 30 | BGlcNAc | GlcNAcβ1 | 0 | 205 | 0 |
| 30 | [6S]BGlcNAc | (6OSO3)GlcNAcβ1 | 0 | 318 | 0 |
| 30 | αMan | Manα1 | 0 | 0 | 0 |
| 30 | βMan | Manβ1 | 0 | 0 | 0 |
| 30 | [6P]Man | (6OPO4)Manα1 | 0 | 0 | 0 |
| 30 | Core3 | GlcNAcβ1-3GalNAcα1 | 0 | 0 | 0 |
| 30 | Core4 | GlcNAcβ1-3(GlcNAcβ1-6)GalNAcα1 | 0 | 0 | 0 |
| 30 | Forssman disaccharide | GalNAcα1-3GalNAcβ | 0 | 0 | 0 |
| 30 | Core6 | GlcNAcβ1-6GalNAcα1 | 0 | 0 | 0 |
| 30 | Core8 | Galα1-3GalNAcα1 | 0 | 0 | 0 |
| 30 | [3'S]Core1 | (3OSO3)Galβ1-3GalNAcα1 | 0 | 0 | 0 |
| 30 | Galβ-Core3 | Galβ1-4GlcNAcβ1-3GalNAcα1 | 0 | 0 | 0 |
| 30 | STn (Gc) | Neu5Gcα2-6GalNAcα1 | 0 | 0 | 0 |
| 30 | ST | Neu5Acα2-3Galβ1-3GalNAcα1 | 0 | 0 | 0 |
| 30 | Siaα2-6Core 1 | Galβ1-3(Neu5Acα2-6)GalNAcα1 | 0 | 0 | 0 |

TABLE 7-continued

Analysis of Clec10a-Fc by glycan microarray

| Rank | Glycan | Structure | Clec10a-Fc | human IgG1 | Clec10a-Fc with EDTA |
|---|---|---|---|---|---|
| | | | | Signal value | |
| 30 | αGlc | Glcα1 | 0 | 0 | 0 |
| 30 | βGlc | Glcβ1 | 0 | 0 | 0 |
| 30 | Maltose | Glcα1-4Glcβ1 | 0 | 0 | 1 |
| 30 | αRha | Rhamnose 1 | 0 | 0 | 0 |
| 30 | Chitobiose | GlcNAcβ1-4GlcNAcβ1 | 0 | 0 | 0 |
| 30 | Negative PAA | — | 0 | 0 | 0 |
| 51 | TxLcl | Galactosylated N-glycans up to triantenna | 973 | 0 | 0 |
| 52 | rDiscoidin I | Gal | 737 | 0 | 0 |
| 53 | rCalsepa | Biantenna with bisecting GlcNAc | 651 | 0 | 0 |
| 54 | rGal3C | LacNAc, polylactosamine | 630 | 0 | 0 |
| 55 | WGA | (GlcNAc)n, polySia | 624 | 0 | 0 |
| 56 | PSA | α1-6Fuc up to biantenna | 481 | 0 | 0 |
| 57 | AOL | α1-2Fuc (H), α1-3Fuc (Lex), α1-3Fuc (Lea) | 309 | 0 | 0 |
| 58 | LCA | α1-6Fuc up to biantenna | 228 | 0 | 0 |
| 59 | rPAIIL | αMan, α1-2Fuc (H), α1-3Fuc (Lex), α1-4Fuc (Lea) | 131 | 0 | 0 |
| 60 | TJAI | α2-6Sia | 113 | 0 | 0 |
| 61 | rBanana | Manα1-2Mana1-3(6)Man | 10 | 0 | 0 |
| 62 | ASA | Galβ1-4GlcNAcβ1-2Man | 2 | 0 | 0 |
| 62 | rCGL3 | LacDiNAc | | 2 | 0 |
| 64 | LFA | Sia | | 0 | 0 |
| 64 | MAL | α2-3Sia | 0 | 0 | 0 |
| 64 | MAH | α2-3Sia | 0 | 0 | 0 |
| 64 | ACG | α2-3Sia | 0 | 0 | 0 |
| 64 | rGal8N | α2-3Sia | 0 | 0 | 0 |
| 64 | SNA | α2-3Sia | 0 | 0 | 0 |
| 64 | ADA | α2-6Sia, Forssman, A, B | 0 | 0 | 0 |
| 64 | PHAL | GlcNAcβ1-6Man (Tetraantenna) | 0 | 0 | 0 |
| 64 | rGal7 | Type 1 LacNAc, chondroitin polymer | 0 | 0 | 0 |
| 64 | rC14 | Branched LacNAc | | 0 | 0 |
| 64 | PHAE | bisecting GlcNAc | | 0 | 0 |
| 64 | GSLII | GlcNAcβ1-4Man | 0 | 0 | 0 |
| 64 | PWM | (GlcNAc)n | 0 | 0 | 0 |
| 64 | rF17AG | GlcNAc | | 0 | 0 |
| 64 | ConA | M3, Manα1-2Manα1-3(Manα1-6)Man, GlcNAcβ1-2Manα1-3(Manα1-6)Man | 0 | 0 | 0 |
| 64 | Heltuba | Manα1-3Man | 0 | 0 | 0 |
| 64 | rHeltuba | Manα1-3Man | 0 | 0 | 0 |
| 64 | WAJI | Man, agalacto | 0 | 0 | 0 |
| 64 | rOryaaia | Manα1-3Man, Highman, biantenna | 0 | 0 | 0 |
| 64 | rRSL | αMan, α1-2Fuc (H), α1-3Fuc (Lex), α1-4Fuc (Lea) | 0 | 0 | 0 |
| 64 | rPTL | α1-6Fuc | 0 | 0 | 0 |
| 64 | LTL | Lex, Ley | 0 | 0 | 0 |
| 64 | UEAI | α1-2Fuc | 0 | 0 | 0 |
| 64 | FLAG-EW29Ch | Gal | | 0 | 0 |
| 64 | PTLI | αGalNAc (A, Tn) | 0 | 0 | 0 |
| 64 | GSLIB4 | αGal (B) | 0 | 0 | 0 |
| 64 | EEL | αGal (B) | 0 | 0 | 0 |
| 64 | rPAIL | α, βGal, αGalNAc (Tn) | 0 | 0 | 0 |
| 64 | DBA | α, βGalNAc (A, Tn, LacDiNAc) | 0 | 0 | 0 |
| 64 | DBA1J | Maltose | 0 | 0 | 0 |
| 64 | rMalectin | Glcα1-2Glc | 0 | 0 | 0 |
| 64 | CSA | Rhamnose, Galα1-4Gal | 0 | 0 | 0 |
| 64 | FLAG-EW20Ch-E20K | 6-sulfo-Gal | 0 | 0 | 0 |

55

Example 4: Relationship Between Human Asgr1 and Mouse Clec10a

Figure 4:
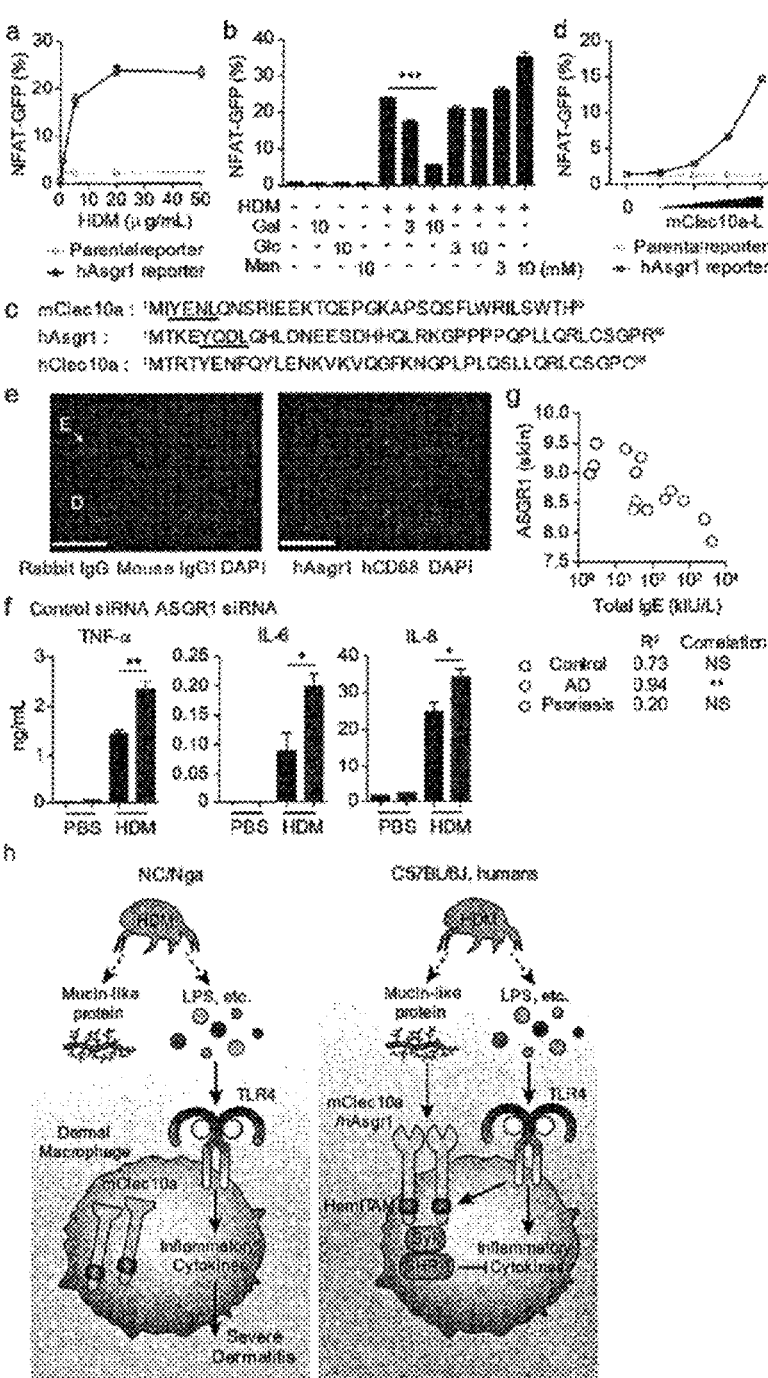
FIG. 4 shows that human Asgr1 is a structural and functional counterpart of mouse Clec10a. Panels a and b show expression of GFP in human Asgr1-CD3 reporter cells after stimulation with HDM-coated plates in the absence of galactose, glucose or mannose (panel a) or in the presence thereof (panel b) (n=3). Panel c shows amino acid sequences of intracellular regions of mouse Clec10a, human Asgr1, and human Clec10a. Deduced hemItAM sequences are underlined. Panel d shows GFP expression in human Asgr1-CD3ζ reporter cells stimulated with Clec10a ligand-coated plates obtained by pulling down from HDM with mouse Clec10a-Fc. Panel e shows results of staining tissue sections of human skin with anti-Asgr1 antibodies, anti-CD68 mAbs and DAPI. E means the epidermis, and D means the dermis. The scale bar indicates 100 μm. Panel f shows results of cytometric bead array (CBA) analysis of culture supernatants from human CD14+ monocyte-derived MP treated with siRNA specific for ASGR1 or control siRNA and stimulated with 100 μg/mL HDM for 6 hours (n=3). Panel g shows correlation of ASGR1 expression (GSE5667) in the skin of healthy subjects, psoriasis patients, and atopic dermatitis patients with serum IgE value. Panel h shows a hypothetical model of a function of a C-type lectin receptor during homeostasis of the skin upon exposure to HDM in mice and humans * represents $p<0.05$,  represents $p<0.01$ and * represents $p<0.001$ (one-sided ANOVA test (panel b), independent two-sided Student's t-test (panel f) or two-sided Pearson correlation test (panel g)). Data indicates mean±SEM.
Figure 9:
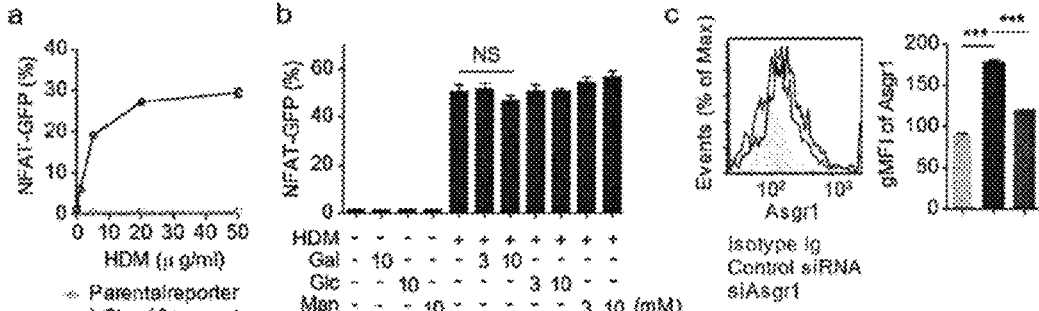
FIG. 9 shows results of HDM stimulation of human Clec10a-CD3ζ reporter cells and knockdown efficiency of human ASGR1. Panels a and b show expression of GFP in human Clec10a-CD3ζ reporter cells after stimulation with HDM-coated plates in the absence (panel a) or presence (panel b) of galactose (Gal), glucose (Glc), or mannose (Man). Panel c shows expression of Asgr1 on the cell surface of human CD14⁺ monocyte-derived MPs treated with control siRNA or siRNA specific for ASGR1. A shaded histogram shows staining with an isotype control antibody. *** represents p<0.001 (one-sided ANOVA test). Data indicates mean±SEM (n=3).

According to Basic Local Alignment Search Tool (BLAST), which is a tool for analyzing amino acid sequence homology and is provided by the National Center for Biotechnology Information (NCBI), in the amino acid sequences of mouse Clec10a and C-type lectin-like domain (CTLD), the human proteins with the highest homology were human Asgr1 and Clec10a (encoded by Gene ID: 432 and 10462, respectively) Human Asgr1 reporter cells and human Clec10a reporter cells expressed GFP in response to HDM stimulation (see panel a in FIG. 4 and panel a in FIG. 9), the addition of galactose inhibited the expression of GFP induced by HDM only in the Asgr1 reporter cells (see panel b in FIG. 4 and panel b in FIG. 9). The hemITAM sequence (YxxL) was not found in human Clec10a and could only be found in human Asgr1 (see panel c in FIG. 4). These results indicate that the functional structural counterpart of Clec10a in mice is not human Clec10a but human Asgr1. The human Asgr1 reporter cells expressed GFP in response to the ligand (Clec10a-L) for mouse Clec10a in HDM (see panel d in FIG. 4). Upon confirmation of protein expression, human Asgr1 expressed in MP in the human skin, similarly to Clec10a expression in the mouse skin (see panel e in FIG. 4). Knockdown of Asgr1 in human mononuclear cell-derived culture MP by siRNA enhanced secretion of inflammatory cytokines in response to HDM (see panel f in FIG. 4, and FIG. 9). This suggests that Asgr1 controls HDM-induced dermatitis in humans. In addition, transcriptional data (GSE5667) showed a reverse correlation between expression of Asgr1 in the skin and the serum IgE level associated with the sensitivity to HDM, in patients with allergic dermatitis (see panel g in FIG. 4). From these results, it was understood that C-type lectin receptors such as Asgr1 in humans and Clec10a in mice recognize mucin-like proteins in HDM and play an important role in maintaining skin homeostasis against HDM-induced inflammation (see panel h in FIG. 4).

Example 5: Treatment of Allergic Symptom with Clec10a Ligand

The results of the previous Examples showed that Clec10a (Asgr1 in humans) is involved in control of HDM-induced allergic symptoms, indicating that ligand stimulation to Clec10a (Asgr1 in humans) is involved in suppression of allergic symptoms. In this Example, allergic symptoms were treated with ligands for Clec10a and the results were observed.

In the first induction (Day 0), the hairs of the dorsal skin of anesthetized mice (C57BL/6J WT) and Clec10a$^{-/-}$ mice) were removed using an electronic clipper, and the remaining hair was epilated using hair removal cream. After tape stripping to the skin in the shaved back, 50 µg LPS was topically administered in the presence or absence of Clec10a-L. The Clec10a ligand was obtained in the manner as described in the above (12) Isolation of Clec10a ligand. The procedures after tape stripping were repeated daily. This induced dermatitis. Epidermal thickness analysis was performed on Day 5 after administration and neutrophil infiltration analysis was performed 6 hours after administration. In this system, TLR4-induced dermatitis was induced.

To observe induced dermatitis, tissue sections were made by a routine method and hematocylin-Eosin staining was performed. Thereafter, the epidermal thickness and the number of neutrophils in the skin were counted.

Figure 10:
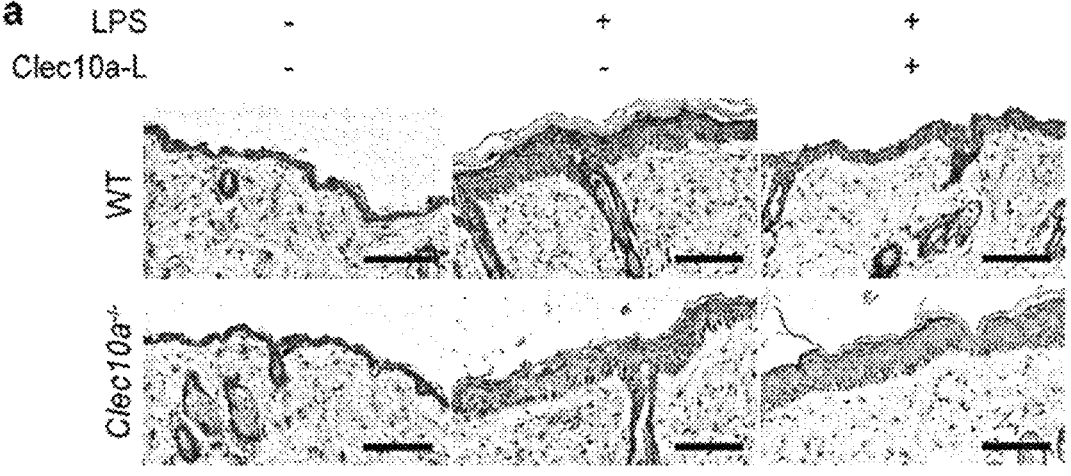
FIG. 10 is a representation illustrating that a Clec10a ligand (Clec10a-L) improves LPS induced dermatitis. Panels a and b show tissue and epidermal thickness, respectively, on Day 5 after daily application of LPS to the dorsal skin of C57BL/6J wild type (wt) mice and Clec10a⁻/⁻ mice in the presence or absence of Clec10a-L. Panel c shows the number (/cm²) of neutrophils (CD45⁺CD11b⁺Ly-6G⁺) in the skin of WT and Clec10a⁻/⁻ mice, 6 hours after LPS was applied to the dorsal skin in the presence or absence of Clec10a-L. * represents p<0.05, and ** represents p<0.01 (independent two-sided Student's t-test). Data indicates mean±SEM.
Figure 10:
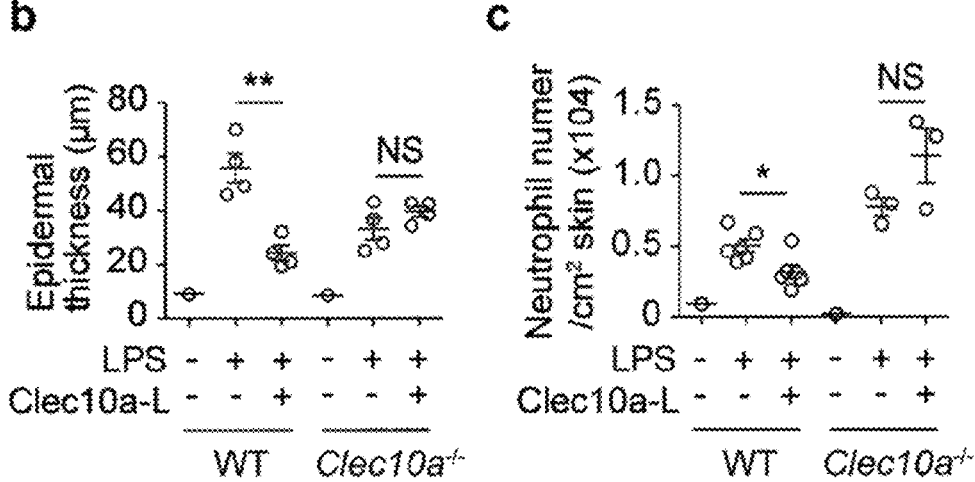

The results were as shown in FIG. 10. In the skin treated with LPS as shown in panel a in FIG. 10, dermatitis was induced and a trend was observed to increase the epidermal thickness (middle photograph). On the other hand, in the wild type mice administered with the Clec10a ligand, the epidermal thickness was significantly reduced (upper right photograph), and the effect of LPS for increasing the epidermal thickness was suppressed. In contrast, in the Clec10a$^{-/-}$ mice, the effect of LPS for increasing the epidermal thickness was observed, but administration of the Clec10a ligand could not suppress the effect for increasing the epidermal thickness. In panel b in FIG. 10, the epidermal thickness is graphed. In FIG. 10, panel b also shows the same results as those in panel a in FIG. 10. Neutrophil infiltration against skin tissue was observed by a routine method. The results, as shown in panel c in FIG. 10, observed neutrophil infiltration in the LPS-treated group in the wild type (WT) mice but neutrophil infiltration was suppressed in the group treated with the Clec10a ligand in addition to LPS. In contrast, in the Clec10a$^{-/-}$ mice, neutrophil infiltration could not be suppressed by the Clec10a ligand. These results revealed that the Clec10a ligand showed a suppressive effect for dermatitis.

HDM is known to contain a TLR4 ligand, which is believed to induce inflammatory and allergic symptoms, such as dermatitis. It is considered that, even in HDM stimulation, the Clec10a ligand binds to Clec10a (in humans, the Asgr1 ligand binds to its functional counterpart, Asgr1) and suppresses a TLR4 signal, resulting in an alleviation effect for inflammatory symptoms and allergic symptoms.

Example 6: Detection of Human Asgr1 Ligand

Figure 11:
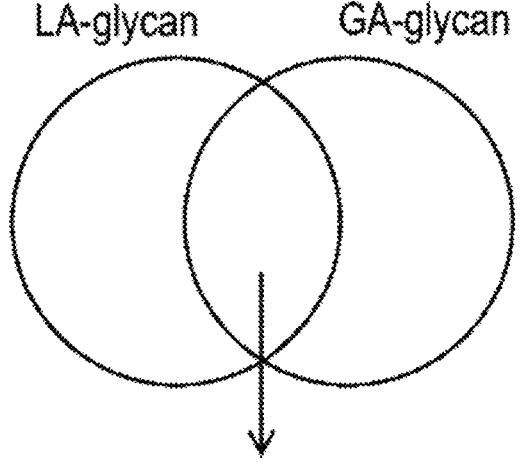
FIG. 11 illustrates a scheme for determining Clec10a-L.
Figure 11:

FIG. 11 shows a scheme for determining the binding profile of Clec10a-L to a lectin by a lectin array and predicting the glycan structure in Clec10a-L (upper left panel in FIG. 11), and a scheme for determining a binding profile of a glycan to Clec10a by a glycan array (upper right panel in FIG. 11). FIG. 11 shows that five glycans (αGal, βGal, T antigen, LeA, and LeX) can be identified as ligand candidates for Clec10a, considering these results together. In FIG. 11, Galα1-3LN and Galα1-4LN were added, and seven Clec10a ligand candidates were identified.

An ELISA system with Clec10a applied to glycan-coated plates was constructed by a routine method to study the binding of each glycan with Clec10a. In the ELISA system, with the expectation that a multivalent effect is achieved by binding a plurality of glycans to the polymeric scaffold, the glycans were bound to the polymeric scaffold and presented to Clec10a. In this example, polyacrylamide (weight average molecular weight: 30 kDa) was used as the polymeric scaffold. Specifically, the glycans were modified with respect to the OH groups of the polyacrylamide side chains as follows, thereby presenting the glycans to Clec10a. This is as shown in the following formula:

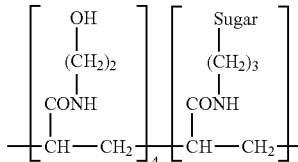

A PBS solution containing 1 µg/well, 0.1 µg/well, or 0.01 µg/well of the polymeric scaffold presenting the glycans at the location "Sugar" of the above formula as described above (the modification rate was 20% as per the above formula) was introduced into a 96 well plate, and incubation was performed overnight at room temperature so that the wells were coated with the glycans. Thereafter, unbound polymer was washed. Subsequently, a 10% fetal bovine serum-containing PBS solution (50 µL/well) containing 1 µg/µl Clec10a-Fc was added to the glycan-coated wells. After 1-hour incubation at room temperature, the unbound Clec10a-Fc was washed, and Clec10a-Fc bound to the plate surface was quantified with peroxidase-labeled anti-Fc antibodies. As a negative object, the polymer described above in which LeY was introduced was used.

Figure 12:
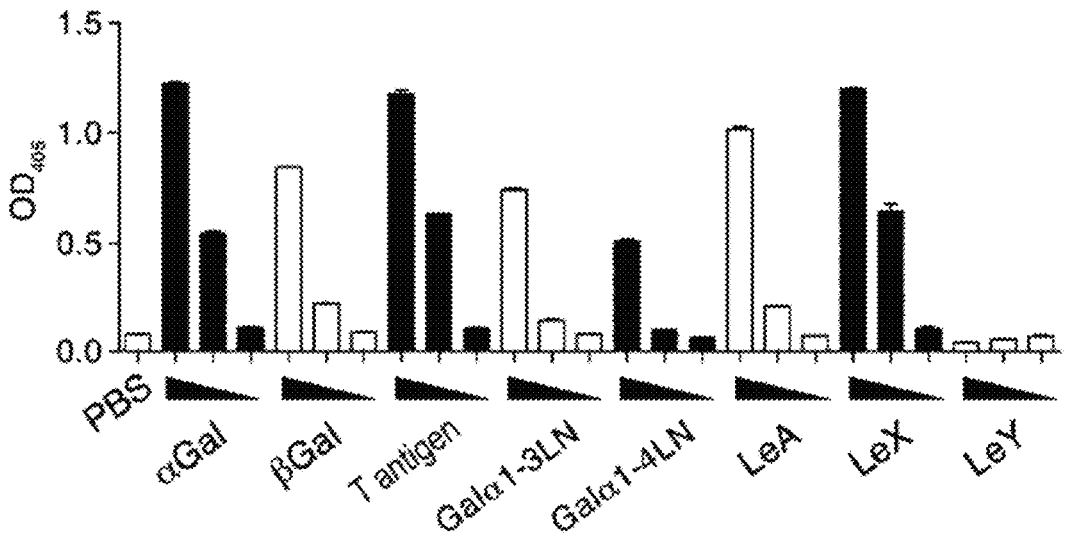
FIG. 12 shows results of an ELISA assay examining whether Clec10a-Fc binds to plates coated with polymeric scaffolds presenting indicated different glycans.

The results were as shown in FIG. 12. As shown in FIG. 12, all of the ligand candidate glycans were bound to Clec10a-Fc. That is, all the ligand candidates were confirmed to be ligands.

Figure 13:
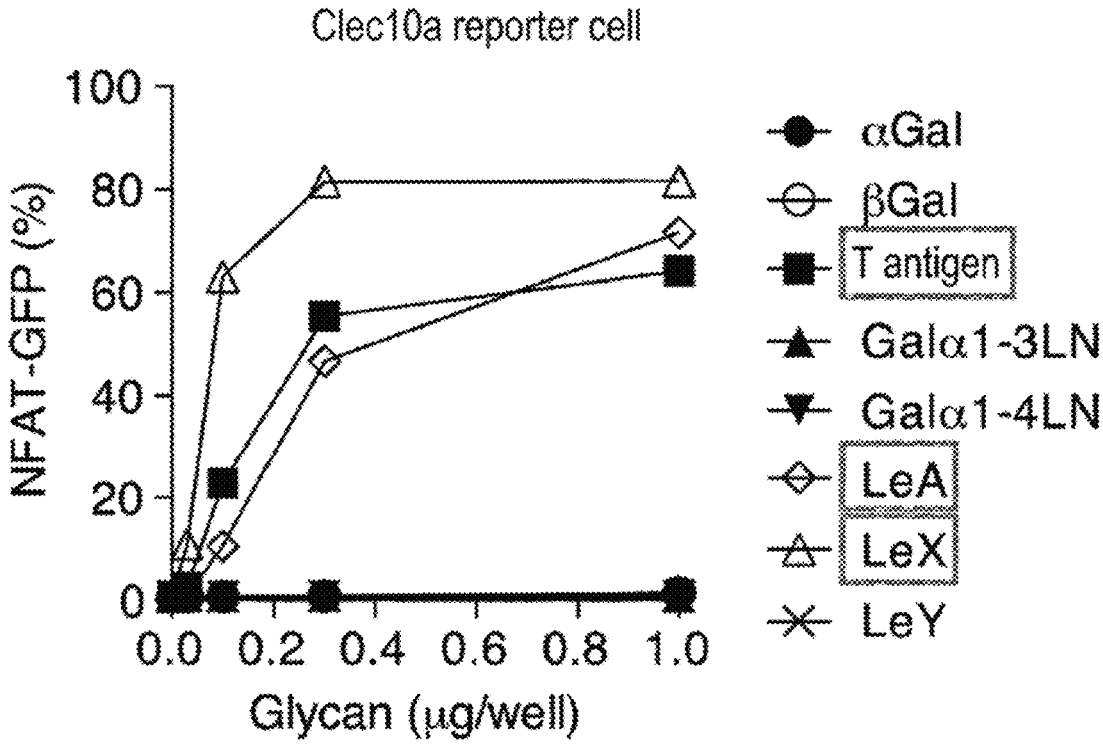

It was confirmed whether these ligands activated Clec10a, using Clec10a-CD3ζ reporter cells. Then, as shown in FIG. 13, the T antigens, LeA, and LeX activated Clec10a in a dose-dependent manner, enhancing expression of the NFAT reporter.

Figure 14:
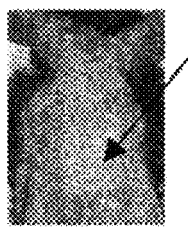
FIG. 14 shows results of a therapeutic experiment examining the effect of administration of polymeric scaffolds presenting T antigens on epidermal inflammation caused by LPS.
Figure 14:
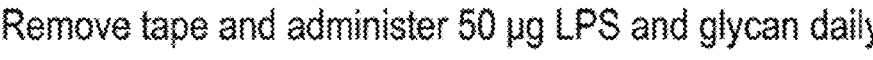
Figure 14:
Figure 14:
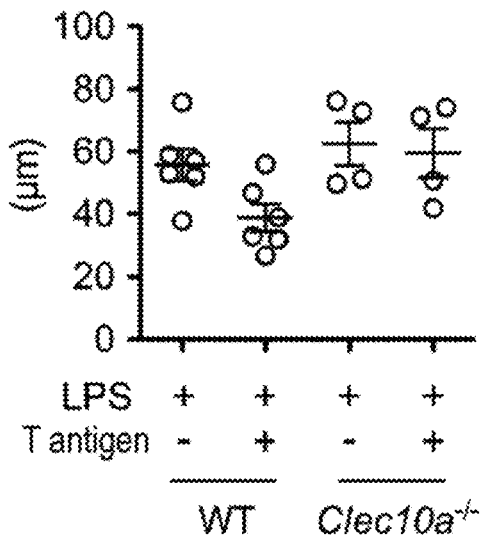

The above experiments revealed Clec10a-activating glycans. It was examined whether one of them, T antigen, could suppress skin inflammation against lipopolysaccharides (LPS). The polymeric scaffolds presenting 50 μg LPS and 20 μg T antigen were intradermally injected in the mouse back daily and the epidermal thickness was observed on Day 5. The results were as shown in FIG. 14. As shown in FIG. 14, increase in thickness of the skin by LPS was suppressed by the T antigen. In the Clec10a-knockout mice, the epidermal thickness was equal to or greater than that in the WT. Here, since the epidermal thickness suppressive effect of the T antigen was not observed in Clec10a knockout mice, it was found that the inflammation suppressive effect of the T antigen is via Clec10a.

SEQUENCE LISTING

[Final] PT37-9002WO_ST25.txt

---

The invention claimed is:

1. A method of treating an allergic disease, comprising:
administering a composition comprising a ligand for asialoglycoprotein receptor 1 (Asgr1) to a subject in need thereof.

2. The method of claim 1, wherein the allergic disease is at least one selected from the group consisting of atopic dermatitis, allergic rhinitis, urticaria, allergic asthma, allergic conjunctivitis, allergic gastrointestinal inflammation, and anaphylactic shock.

3. The method of claim 1, wherein the allergic disease is caused by a house dust mite.

4. The method of claim 1, wherein the subject is a human.

5. The method of claim 1, wherein the ligand comprises a polymeric scaffold presenting at least one glycan selected from the group consisting of a T antigen, a Tn antigen, and LeA, provided that the ligand is neither mucin nor a mucin-like protein and does not contain LeX.

6. The method of claim 5, wherein the polymeric scaffold comprises at least one polymer selected from the group consisting of polylactic acid, polyacrylamide, polyvinyl, polyvinyl alcohol, polymethyl methacrylate, polyacrylonitrile, polystyrene, polypropylene, polyethylene terephthalate, nylon, collagen, hydroxyethyl methacrylate, chitosan, chitin, polyethylene oxide, polyethylene glycol, polyamino acid, polylactide, polyglycolide, polycaprolactone, and a copolymer thereof.

7. The method of claim 1, wherein the composition is in a form of a gel, an emulsion, a cream, a liquid, a paste, a lotion, or a liposome cream.

8. The method of claim 1, wherein the composition further comprises an effective amount of a pharmaceutically acceptable additive.

9. The method of claim 8, wherein the pharmaceutically acceptable additive is at least one selected from the group consisting of a solvent, a base, a diluent, a volume filler, and an auxiliary.

10. The method of claim 8, wherein the pharmaceutically acceptable additive is at least one selected from the group consisting of a dissolution aid, a solubilizer, a buffer, an isotonizing agent, an emulsifier, a suspending agent, a dispersant, a thickener, a gelling agent, a curing agent, an absorbent, an adhesive, an elastic agent, a plasticizer, a sustained release agent, and a propellant.

11. The method of claim 1, wherein the ligand positively regulates a downstream signal of asialoglycoprotein receptor 1 (Asgr1) by binding to the receptor.

12. The method of claim 1, wherein the ligand comprises at least one glycan selected from the group consisting of a T antigen, a Tn antigen and LeA, and positively regulates a downstream signal of asialoglycoprotein receptor 1 (Asgr1) by binding thereto, provided that the ligand is neither mucin nor a mucin-like protein and does not contain LeX.

*     *     *     *     *

```
                      SEQUENCE LISTING

<160> NUMBER OF SEQ ID NOS: 76

<210> SEQ ID NO 1
<211> LENGTH: 20
<212> TYPE: DNA
<213> ORGANISM: Artificial Sequence
<220> FEATURE:
<223> OTHER INFORMATION: Clec10a Forward primer

<400> SEQUENCE: 1
acccaagagc ctggtaaagc                                              20

<210> SEQ ID NO 2
<211> LENGTH: 20
<212> TYPE: DNA
<213> ORGANISM: Artificial Sequence
<220> FEATURE:
<223> OTHER INFORMATION: Clec10a Reverse primer

<400> SEQUENCE: 2
gatccaatca cggagacgac                                              20

<210> SEQ ID NO 3
<211> LENGTH: 17
<212> TYPE: DNA
<213> ORGANISM: Artificial Sequence
<220> FEATURE:
<223> OTHER INFORMATION: Tnf Forward primer

<400> SEQUENCE: 3
gggccaccac gctcttc                                                 17

<210> SEQ ID NO 4
<211> LENGTH: 22
<212> TYPE: DNA
<213> ORGANISM: Artificial Sequence
<220> FEATURE:
<223> OTHER INFORMATION: Tnf Reverse primer

<400> SEQUENCE: 4
ggtctgggcc atagaactga tg                                           22

<210> SEQ ID NO 5
<211> LENGTH: 23
<212> TYPE: DNA
<213> ORGANISM: Artificial Sequence
<220> FEATURE:
<223> OTHER INFORMATION: Il6 Forward primer

<400> SEQUENCE: 5
gaggatacca ctcccaacag acc                                          23

<210> SEQ ID NO 6
<211> LENGTH: 24
<212> TYPE: DNA
<213> ORGANISM: Artificial Sequence
```

-continued

```
<220> FEATURE:
<223> OTHER INFORMATION: Il6 Reverse primer

<400> SEQUENCE: 6
aagtgcatca tcgttgttca taca                                          24

<210> SEQ ID NO 7
<211> LENGTH: 20
<212> TYPE: DNA
<213> ORGANISM: Artificial Sequence
<220> FEATURE:
<223> OTHER INFORMATION: Cxcl1 Forward primer

<400> SEQUENCE: 7
actcaagaat ggtcgcgagg                                               20

<210> SEQ ID NO 8
<211> LENGTH: 20
<212> TYPE: DNA
<213> ORGANISM: Artificial Sequence
<220> FEATURE:
<223> OTHER INFORMATION: Cxcl1 Reverse primer

<400> SEQUENCE: 8
gtgccatcag agcagtctgt                                               20

<210> SEQ ID NO 9
<211> LENGTH: 20
<212> TYPE: DNA
<213> ORGANISM: Artificial Sequence
<220> FEATURE:
<223> OTHER INFORMATION: Cxcl2 Forward primer

<400> SEQUENCE: 9
aagtttgcct tgaccctgaa                                               20

<210> SEQ ID NO 10
<211> LENGTH: 20
<212> TYPE: DNA
<213> ORGANISM: Artificial Sequence
<220> FEATURE:
<223> OTHER INFORMATION: Cxcl2 Reverse primer

<400> SEQUENCE: 10
aggcacatca ggtacgatcc                                               20

<210> SEQ ID NO 11
<211> LENGTH: 21
<212> TYPE: DNA
<213> ORGANISM: Artificial Sequence
<220> FEATURE:
<223> OTHER INFORMATION: Ifng Forward primer

<400> SEQUENCE: 11
acagcaaggc gaaaaaggat g                                             21

<210> SEQ ID NO 12
<211> LENGTH: 19
<212> TYPE: DNA
<213> ORGANISM: Artificial Sequence
<220> FEATURE:
<223> OTHER INFORMATION: Ifng Reverse primer

<400> SEQUENCE: 12
tggtggacca ctcggatga                                                19
```

-continued

```
<210> SEQ ID NO 13
<211> LENGTH: 22
<212> TYPE: DNA
<213> ORGANISM: Artificial Sequence
<220> FEATURE:
<223> OTHER INFORMATION: Il4 Forward primer

<400> SEQUENCE: 13
atcatcggca ttttgaacga gg                                              22

<210> SEQ ID NO 14
<211> LENGTH: 21
<212> TYPE: DNA
<213> ORGANISM: Artificial Sequence
<220> FEATURE:
<223> OTHER INFORMATION: Il4 Reverse primer

<400> SEQUENCE: 14
tgcagctcca tgagaacact a                                               21

<210> SEQ ID NO 15
<211> LENGTH: 21
<212> TYPE: DNA
<213> ORGANISM: Artificial Sequence
<220> FEATURE:
<223> OTHER INFORMATION: Il17 Forward primer

<400> SEQUENCE: 15
tttaactccc ttggcgcaaa a                                               21

<210> SEQ ID NO 16
<211> LENGTH: 20
<212> TYPE: DNA
<213> ORGANISM: Artificial Sequence
<220> FEATURE:
<223> OTHER INFORMATION: Il17 Reverse primer

<400> SEQUENCE: 16
ctttccctcc gcattgacac                                                 20

<210> SEQ ID NO 17
<211> LENGTH: 22
<212> TYPE: DNA
<213> ORGANISM: Artificial Sequence
<220> FEATURE:
<223> OTHER INFORMATION: Il10 Forward primer

<400> SEQUENCE: 17
gctggacaac atactgctaa cc                                              22

<210> SEQ ID NO 18
<211> LENGTH: 21
<212> TYPE: DNA
<213> ORGANISM: Artificial Sequence
<220> FEATURE:
<223> OTHER INFORMATION: Il10 Reverse primer

<400> SEQUENCE: 18
atttccgata aggcttggca a                                               21

<210> SEQ ID NO 19
<211> LENGTH: 19
<212> TYPE: DNA
<213> ORGANISM: Artificial Sequence
<220> FEATURE:
<223> OTHER INFORMATION: Tbx21 Forward primer
```

-continued

```
<400> SEQUENCE: 19
agcaaggacg gcgaatgtt                                              19

<210> SEQ ID NO 20
<211> LENGTH: 21
<212> TYPE: DNA
<213> ORGANISM: Artificial Sequence
<220> FEATURE:
<223> OTHER INFORMATION: Tbx21 Reverse primer

<400> SEQUENCE: 20
gggtggacat ataagcggtt c                                           21

<210> SEQ ID NO 21
<211> LENGTH: 20
<212> TYPE: DNA
<213> ORGANISM: Artificial Sequence
<220> FEATURE:
<223> OTHER INFORMATION: Gata3 Forward primer

<400> SEQUENCE: 21
ttatcaagcc caagcgaagg                                             20

<210> SEQ ID NO 22
<211> LENGTH: 22
<212> TYPE: DNA
<213> ORGANISM: Artificial Sequence
<220> FEATURE:
<223> OTHER INFORMATION: Gata3 Reverse primer

<400> SEQUENCE: 22
cattagcgtt cctcctccag ag                                          22

<210> SEQ ID NO 23
<211> LENGTH: 20
<212> TYPE: DNA
<213> ORGANISM: Artificial Sequence
<220> FEATURE:
<223> OTHER INFORMATION: Rorc Forward primer

<400> SEQUENCE: 23
ggaggacagg gagccaagtt                                             20

<210> SEQ ID NO 24
<211> LENGTH: 22
<212> TYPE: DNA
<213> ORGANISM: Artificial Sequence
<220> FEATURE:
<223> OTHER INFORMATION: Rorc Reverse primer

<400> SEQUENCE: 24
ccgtagtgga tcccagatga ct                                          22

<210> SEQ ID NO 25
<211> LENGTH: 19
<212> TYPE: DNA
<213> ORGANISM: Artificial Sequence
<220> FEATURE:
<223> OTHER INFORMATION: Foxp3 Forward primer

<400> SEQUENCE: 25
cccatcccca ggagtcttg                                              19

<210> SEQ ID NO 26
```

```
<211> LENGTH: 21
<212> TYPE: DNA
<213> ORGANISM: Artificial Sequence
<220> FEATURE:
<223> OTHER INFORMATION: Foxp3 Reverse primer

<400> SEQUENCE: 26
accatgacta ggggcactgt a                                               21

<210> SEQ ID NO 27
<211> LENGTH: 20
<212> TYPE: DNA
<213> ORGANISM: Artificial Sequence
<220> FEATURE:
<223> OTHER INFORMATION: Gapdh Forward primer

<400> SEQUENCE: 27
tggtgaaggt cggtgtgaac                                                 20

<210> SEQ ID NO 28
<211> LENGTH: 20
<212> TYPE: DNA
<213> ORGANISM: Artificial Sequence
<220> FEATURE:
<223> OTHER INFORMATION: Gapdh Reverse primer

<400> SEQUENCE: 28
atgaaggggt cgttgatggc                                                 20

<210> SEQ ID NO 29
<211> LENGTH: 20
<212> TYPE: DNA
<213> ORGANISM: Artificial Sequence
<220> FEATURE:
<223> OTHER INFORMATION: Cdh20 Forward primer

<400> SEQUENCE: 29
tcggactcag agcagagctt                                                 20

<210> SEQ ID NO 30
<211> LENGTH: 20
<212> TYPE: DNA
<213> ORGANISM: Artificial Sequence
<220> FEATURE:
<223> OTHER INFORMATION: Cdh20 Reverse primer

<400> SEQUENCE: 30
ctctgctggg tccactcact                                                 20

<210> SEQ ID NO 31
<211> LENGTH: 20
<212> TYPE: DNA
<213> ORGANISM: Artificial Sequence
<220> FEATURE:
<223> OTHER INFORMATION: Tlr5 Forward primer

<400> SEQUENCE: 31
gccattcttc cttgaaccac                                                 20

<210> SEQ ID NO 32
<211> LENGTH: 20
<212> TYPE: DNA
<213> ORGANISM: Artificial Sequence
<220> FEATURE:
<223> OTHER INFORMATION: Tlr5 Reverse primer

<400> SEQUENCE: 32
```

```
atggccgtgt gggagtataa                                    20

<210> SEQ ID NO 33
<211> LENGTH: 20
<212> TYPE: DNA
<213> ORGANISM: Artificial Sequence
<220> FEATURE:
<223> OTHER INFORMATION: Tmem141 Forward primer

<400> SEQUENCE: 33
gatcagggac tccaaaacca                                    20

<210> SEQ ID NO 34
<211> LENGTH: 20
<212> TYPE: DNA
<213> ORGANISM: Artificial Sequence
<220> FEATURE:
<223> OTHER INFORMATION: Tmem141 Reverse primer

<400> SEQUENCE: 34
tgctgaggta ggagggactg                                    20

<210> SEQ ID NO 35
<211> LENGTH: 20
<212> TYPE: DNA
<213> ORGANISM: Artificial Sequence
<220> FEATURE:
<223> OTHER INFORMATION: Qsox2 Forward primer

<400> SEQUENCE: 35
agactcagcc acgtgaacct                                    20

<210> SEQ ID NO 36
<211> LENGTH: 20
<212> TYPE: DNA
<213> ORGANISM: Artificial Sequence
<220> FEATURE:
<223> OTHER INFORMATION: Qsox2 Reverse primer

<400> SEQUENCE: 36
tcgggctcag acatttcact                                    20

<210> SEQ ID NO 37
<211> LENGTH: 25
<212> TYPE: DNA
<213> ORGANISM: Artificial Sequence
<220> FEATURE:
<223> OTHER INFORMATION: Hc Forward primer

<400> SEQUENCE: 37
tcgtgttttt aaatattttg cttcc                              25

<210> SEQ ID NO 38
<211> LENGTH: 20
<212> TYPE: DNA
<213> ORGANISM: Artificial Sequence
<220> FEATURE:
<223> OTHER INFORMATION: Hc Reverse primer

<400> SEQUENCE: 38
ccccaccctc ttctggtact                                    20

<210> SEQ ID NO 39
<211> LENGTH: 20
<212> TYPE: DNA
```

-continued

```
<213> ORGANISM: Artificial Sequence
<220> FEATURE:
<223> OTHER INFORMATION: Tdpoz2 Forward primer

<400> SEQUENCE: 39
ggtggaagtc aatggtggag                                                   20

<210> SEQ ID NO 40
<211> LENGTH: 21
<212> TYPE: DNA
<213> ORGANISM: Artificial Sequence
<220> FEATURE:
<223> OTHER INFORMATION: Tdpoz2 Reverse primer

<400> SEQUENCE: 40
ttgtctctgg gactcaaagg a                                                 21

<210> SEQ ID NO 41
<211> LENGTH: 20
<212> TYPE: DNA
<213> ORGANISM: Artificial Sequence
<220> FEATURE:
<223> OTHER INFORMATION: Gm572 Forward primer

<400> SEQUENCE: 41
gtttcggcgc ttttgtttta                                                   20

<210> SEQ ID NO 42
<211> LENGTH: 20
<212> TYPE: DNA
<213> ORGANISM: Artificial Sequence
<220> FEATURE:
<223> OTHER INFORMATION: Gm572 Reverse primer

<400> SEQUENCE: 42
cttcagaggc caggacaaag                                                   20

<210> SEQ ID NO 43
<211> LENGTH: 22
<212> TYPE: DNA
<213> ORGANISM: Artificial Sequence
<220> FEATURE:
<223> OTHER INFORMATION: Cyp3a57 Forward primer

<400> SEQUENCE: 43
tgatgttctt ctttgacctt cc                                                22

<210> SEQ ID NO 44
<211> LENGTH: 21
<212> TYPE: DNA
<213> ORGANISM: Artificial Sequence
<220> FEATURE:
<223> OTHER INFORMATION: Cyp3a57 Reverse primer

<400> SEQUENCE: 44
tccctctctg agtaccatcc a                                                 21

<210> SEQ ID NO 45
<211> LENGTH: 20
<212> TYPE: DNA
<213> ORGANISM: Artificial Sequence
<220> FEATURE:
<223> OTHER INFORMATION: Try4 Forward primer

<400> SEQUENCE: 45
gagggctcca cctaacaaca                                                   20
```

```
<210> SEQ ID NO 46
<211> LENGTH: 20
<212> TYPE: DNA
<213> ORGANISM: Artificial Sequence
<220> FEATURE:
<223> OTHER INFORMATION: Try4 Reverse primer

<400> SEQUENCE: 46
gtacagacag ggcccatcac                                           20

<210> SEQ ID NO 47
<211> LENGTH: 22
<212> TYPE: DNA
<213> ORGANISM: Artificial Sequence
<220> FEATURE:
<223> OTHER INFORMATION: Klri2 Forward primer

<400> SEQUENCE: 47
tgatgagcac tcatttcaca ca                                        22

<210> SEQ ID NO 48
<211> LENGTH: 20
<212> TYPE: DNA
<213> ORGANISM: Artificial Sequence
<220> FEATURE:
<223> OTHER INFORMATION: Klri2 Reverse primer

<400> SEQUENCE: 48
tcccagtgcc aacagttaca                                           20

<210> SEQ ID NO 49
<211> LENGTH: 22
<212> TYPE: DNA
<213> ORGANISM: Artificial Sequence
<220> FEATURE:
<223> OTHER INFORMATION: Klra7 Forward primer

<400> SEQUENCE: 49
aaagttaaag agttgcccct tg                                        22

<210> SEQ ID NO 50
<211> LENGTH: 23
<212> TYPE: DNA
<213> ORGANISM: Artificial Sequence
<220> FEATURE:
<223> OTHER INFORMATION: Klra7 Reverse primer

<400> SEQUENCE: 50
tgaattattg caggaaacaa atg                                       23

<210> SEQ ID NO 51
<211> LENGTH: 20
<212> TYPE: DNA
<213> ORGANISM: Artificial Sequence
<220> FEATURE:
<223> OTHER INFORMATION: Ttc23 Forward primer

<400> SEQUENCE: 51
gaactgctct aacgctgtgg                                           20

<210> SEQ ID NO 52
<211> LENGTH: 19
<212> TYPE: DNA
<213> ORGANISM: Artificial Sequence
<220> FEATURE:
```

-continued

```
<223> OTHER INFORMATION: Ttc23 Reverse primer

<400> SEQUENCE: 52
acagtgccat ccagggttc                                           19

<210> SEQ ID NO 53
<211> LENGTH: 20
<212> TYPE: DNA
<213> ORGANISM: Artificial Sequence
<220> FEATURE:
<223> OTHER INFORMATION: Olfml1 Forward primer

<400> SEQUENCE: 53
gggcattcat ggaagatagc                                          20

<210> SEQ ID NO 54
<211> LENGTH: 20
<212> TYPE: DNA
<213> ORGANISM: Artificial Sequence
<220> FEATURE:
<223> OTHER INFORMATION: Olfml1 Reverse primer

<400> SEQUENCE: 54
catccacagc aaggtcaatg                                          20

<210> SEQ ID NO 55
<211> LENGTH: 19
<212> TYPE: DNA
<213> ORGANISM: Artificial Sequence
<220> FEATURE:
<223> OTHER INFORMATION: Foxr1 ForwardEprimer

<400> SEQUENCE: 55
cgcagtttcc ccttctcat                                           19

<210> SEQ ID NO 56
<211> LENGTH: 21
<212> TYPE: DNA
<213> ORGANISM: Artificial Sequence
<220> FEATURE:
<223> OTHER INFORMATION: Foxr1 Reverse primer

<400> SEQUENCE: 56
tggaggtaca aggttctgtg c                                        21

<210> SEQ ID NO 57
<211> LENGTH: 20
<212> TYPE: DNA
<213> ORGANISM: Artificial Sequence
<220> FEATURE:
<223> OTHER INFORMATION: Cilp Forward primer

<400> SEQUENCE: 57
aagagcaatg tgggagttgc                                          20

<210> SEQ ID NO 58
<211> LENGTH: 20
<212> TYPE: DNA
<213> ORGANISM: Artificial Sequence
<220> FEATURE:
<223> OTHER INFORMATION: Cilp Reverse primer

<400> SEQUENCE: 58
agcatcatga ggcagagaca                                          20
```

-continued

```
<210> SEQ ID NO 59
<211> LENGTH: 20
<212> TYPE: DNA
<213> ORGANISM: Artificial Sequence
<220> FEATURE:
<223> OTHER INFORMATION: Slc22a21 Forward primer

<400> SEQUENCE: 59
gcttgttttg caactgatgg                                              20

<210> SEQ ID NO 60
<211> LENGTH: 20
<212> TYPE: DNA
<213> ORGANISM: Artificial Sequence
<220> FEATURE:
<223> OTHER INFORMATION: Slc22a21 Reverse primer

<400> SEQUENCE: 60
agcactgttg tcggtcactg                                              20

<210> SEQ ID NO 61
<211> LENGTH: 20
<212> TYPE: DNA
<213> ORGANISM: Artificial Sequence
<220> FEATURE:
<223> OTHER INFORMATION: Clec10a Forward 2 primer

<400> SEQUENCE: 61
tgagggagag gtaaccatgc                                              20

<210> SEQ ID NO 62
<211> LENGTH: 20
<212> TYPE: DNA
<213> ORGANISM: Artificial Sequence
<220> FEATURE:
<223> OTHER INFORMATION: Clec10a Reverse 2

<400> SEQUENCE: 62
gggcaaatgt acagcacaca                                              20

<210> SEQ ID NO 63
<211> LENGTH: 20
<212> TYPE: DNA
<213> ORGANISM: Artificial Sequence
<220> FEATURE:
<223> OTHER INFORMATION: Serpina3i Forward primer

<400> SEQUENCE: 63
gctgtcagga ctcagcagtg                                              20

<210> SEQ ID NO 64
<211> LENGTH: 20
<212> TYPE: DNA
<213> ORGANISM: Artificial Sequence
<220> FEATURE:
<223> OTHER INFORMATION: Serpina3i Reverse primer

<400> SEQUENCE: 64
ggtcagggag aatgaacagg                                              20

<210> SEQ ID NO 65
<211> LENGTH: 20
<212> TYPE: DNA
<213> ORGANISM: Artificial Sequence
<220> FEATURE:
<223> OTHER INFORMATION: Zkscan4 Forward primer
```

-continued

<400> SEQUENCE: 65
aatccacacg ggtgagaaac                                              20

<210> SEQ ID NO 66
<211> LENGTH: 20
<212> TYPE: DNA
<213> ORGANISM: Artificial Sequence
<220> FEATURE:
<223> OTHER INFORMATION: Zkscan4 Reverse primer

<400> SEQUENCE: 66
cagtgtgtat tggccacacc                                              20

<210> SEQ ID NO 67
<211> LENGTH: 20
<212> TYPE: DNA
<213> ORGANISM: Artificial Sequence
<220> FEATURE:
<223> OTHER INFORMATION: Zfp957 Forward primer

<400> SEQUENCE: 67
tgcagagcaa agtcaaggtt                                              20

<210> SEQ ID NO 68
<211> LENGTH: 18
<212> TYPE: DNA
<213> ORGANISM: Artificial Sequence
<220> FEATURE:
<223> OTHER INFORMATION: Zfp957 Reverse primer

<400> SEQUENCE: 68
cttagcggct gcgttttt                                                18

<210> SEQ ID NO 69
<211> LENGTH: 20
<212> TYPE: DNA
<213> ORGANISM: Artificial Sequence
<220> FEATURE:
<223> OTHER INFORMATION: Timm8a2 Forward primer

<400> SEQUENCE: 69
catccaccac atgacagagc                                              20

<210> SEQ ID NO 70
<211> LENGTH: 20
<212> TYPE: DNA
<213> ORGANISM: Artificial Sequence
<220> FEATURE:
<223> OTHER INFORMATION: Timm8a2 Reverse primer

<400> SEQUENCE: 70
gtccatttcc ccacctacct                                              20

<210> SEQ ID NO 71
<211> LENGTH: 20
<212> TYPE: DNA
<213> ORGANISM: Artificial Sequence
<220> FEATURE:
<223> OTHER INFORMATION: Pdzd2 Forward primer

<400> SEQUENCE: 71
atgcatgctc gcttttctt                                               20

<210> SEQ ID NO 72
<211> LENGTH: 20

-continued

```
<212> TYPE: DNA
<213> ORGANISM: Artificial Sequence
<220> FEATURE:
<223> OTHER INFORMATION: Pdzd2 Reverse primer

<400> SEQUENCE: 72
gagggatggg ggaagagtta                                        20

<210> SEQ ID NO 73
<211> LENGTH: 20
<212> TYPE: DNA
<213> ORGANISM: Artificial Sequence
<220> FEATURE:
<223> OTHER INFORMATION: Cyp2d11 Forward primer

<400> SEQUENCE: 73
aggcagagtc caacaggaaa                                        20

<210> SEQ ID NO 74
<211> LENGTH: 20
<212> TYPE: DNA
<213> ORGANISM: Artificial Sequence
<220> FEATURE:
<223> OTHER INFORMATION: Cyp2d11 Reverse primer

<400> SEQUENCE: 74
cctaccttgg tgacgaggaa                                        20

<210> SEQ ID NO 75
<211> LENGTH: 20
<212> TYPE: DNA
<213> ORGANISM: Artificial Sequence
<220> FEATURE:
<223> OTHER INFORMATION: Kcnk7 Forward primer

<400> SEQUENCE: 75
ccccagcctc agtatcagaa                                        20

<210> SEQ ID NO 76
<211> LENGTH: 20
<212> TYPE: DNA
<213> ORGANISM: Artificial Sequence
<220> FEATURE:
<223> OTHER INFORMATION: Kcnk7 Reverse primer

<400> SEQUENCE: 76
atttagccca gagtcgcttg                                        20
```